US009200271B2

(12) United States Patent
Kruglick

(10) Patent No.: US 9,200,271 B2
(45) Date of Patent: Dec. 1, 2015

(54) SELECTIVE 3D BIOPATTERNING

(75) Inventor: Ezekiel Kruglick, Poway, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 13/202,816

(22) PCT Filed: Feb. 3, 2011

(86) PCT No.: PCT/US2011/023633
§ 371 (c)(1),
(2), (4) Date: Aug. 23, 2011

(87) PCT Pub. No.: WO2012/105983
PCT Pub. Date: Aug. 9, 2012

(65) Prior Publication Data
US 2013/0309706 A1 Nov. 21, 2013

(51) Int. Cl.
*C12N 13/00* (2006.01)
*A61L 27/34* (2006.01)
*A61L 27/50* (2006.01)

(52) U.S. Cl.
CPC ............... *C12N 13/00* (2013.01); *A61L 27/34* (2013.01); *A61L 27/50* (2013.01); *A61L 2400/12* (2013.01)

(58) Field of Classification Search
None
See application file for complete search history.

(56) References Cited

U.S. PATENT DOCUMENTS

| | | | | |
|---|---|---|---|---|
| 4,333,165 | A * | 6/1982 | Swainson et al. | 365/120 |
| 6,703,235 | B2 * | 3/2004 | Luebke et al. | 435/283.1 |
| 2006/0240061 | A1 * | 10/2006 | Atala et al. | 424/422 |
| 2008/0187487 | A1 * | 8/2008 | Larsen et al. | 424/1.21 |
| 2008/0206870 | A1 | 8/2008 | Groisman et al. | |
| 2008/0286360 | A1 | 11/2008 | Shoichet et al. | |
| 2009/0247911 | A1 * | 10/2009 | Novak et al. | 601/2 |
| 2010/0093066 | A1 | 4/2010 | Taylor et al. | |
| 2011/0091389 | A1 | 4/2011 | Kruglick | |

FOREIGN PATENT DOCUMENTS

| | | |
|---|---|---|
| JP | 2010088316 | 4/2010 |
| WO | 0056375 | 9/2000 |

OTHER PUBLICATIONS

International Search Report and Written Opinion, issued in International Patent Application No. PCT/US2011/023633, mailed Apr. 21, 2011, 15 pages.
Altinoglu et al., "Near-Infrared Emitting Fluorophore-Doped Calcium Phosphate Nanoparticles for In Vivo Imaging of Human Breast Cancer," ACS Nano, 2008, pp. 2075-2084, vol. 2.
Cai et al., "Ultrasound Controlled Morphology Transformation of Hollow Calcium Phosphate Nanospheres: A Smart and Biocompatible Drug Release System," Chem. Mater., 2007, pp. 3081-3083, vol. 19.
You et al., "Exceptionally High Payload of Doxorubicin in Hollow Gold Nanospheres for Near-infrared Light-triggered Drug Release," ACS Nano, 2010, pp. 1033-1041, vol. 4, No. 2.
Son et al., "Inorganic Hollow Nanoparticles and Nanotubes in Nanomedicine Part 1. Drug/gene Delivery Applications," Drug Disc. Today, 2007, pp. 650-656, vol. 12, No. 15/16.
Chen et al., "DNA-gold Nanorod Conjugates for Remote Control of Localized Gene Expression by Near Infrared Irradiation," J. Am. Chem. Soc., Feb. 2006, pp. 3709-3715, vol. 128, No. 11.
Wijaya et al., "Selective Release of Multiple DNA Oligonucleotides from Gold Nanorods," ACS Nano, 2009, pp. 80-86, vol. 3, No. 1.
Loo et al., "Nanoshell-enabled Photonics-based Imaging and Therapy of Cancer," Tech. in Cancer Res. & Treat, Feb. 2004, pp. 33-40, vol. 3, No. 1.
Ott et al., "Perfusion-decellularized Matrix: Using Nature's Platform to Engineer a Bioartificial Heart," Nature Med., Jan. 2008, pp. 213-221, vol. 14.
John et al., "In vitro Investigations of Bone Remodeling on a Transparent Hydroxyapatite Ceramic," Biomed. Materials, 2009, pp. 1-9, vol. 4, No. 1.
Park et al., "Micropattern-immobilization of Heparin to Regulate Cell Growth with Fibroblast Growth Factor," Cytotechnology, Jul. 2000, pp. 117-122, vol. 33, No. 1.
Dudley et al., "Emerging Digital Micromirror Device (DMD) Applications," Proceedings of the SPIE International Society for Optical Engineering, 2003, pp. 14-25, vol. 4985.
Ito, "Tissue Engineering by Immobilized Growth Factors," Mat. Sci. and Eng. C, Dec. 1998, pp. 267-274, vol. 6, No. 4.
Chen et al., "Photo-immobilization of Epidermal Growth Factor Enhances its Mitogenic Effect by Artificial Juxtacrine Signaling," Biochimica et Biophysica Acta, 1997, pp. 200-208, vol. 1358, No. 2.
Uhrich et al., "Synthesis and Characterization of Degradable Poly(anhydride-co-imides)," Macromolecules, Mar. 1995, pp. 2184-2193, vol. 28, No. 7.
Massachusetts Institute of Technology, "Gold particles and infrared light for controlled drug delivery," News-medical.net, Jan. 1, 2009, 1 page.

(Continued)

*Primary Examiner* — Taeyoon Kim
*Assistant Examiner* — Emily Cordas
(74) *Attorney, Agent, or Firm* — Foley & Lardner LLP

(57) ABSTRACT

Methods, systems, and articles for selective three dimensional (3D) biopatterning are disclosed. A biological target may be imaged and a selected area of the image may define a desired pattern for guiding the emission of EM radiation into the biological target. Two or more groups of photosensitive elements responsive to different activation wavelengths may be provided. The photosensitive elements may be selectively activated on or within the biological target based on location and activation wavelength in order to guide cell differentiation, adhesion of growth factors to a scaffold, release of growth factors, and/or deletion of cells.

15 Claims, 14 Drawing Sheets

(56) References Cited

OTHER PUBLICATIONS

Woo, Y. K, et al., "Proliferation of anterior cruciate ligament cells in vitro by photo-immobilized epidermal growth factor," J. Orthop. Res., Jan. 2007, pp. 73-80, vol. 25, No. 1.

Ito, Y. et al., "Micropatterned immobilization of epidermal growth factor to regulate cell function," Bioconjug. Chem. Mar. 1998, pp. 277-282, vol. 9, No. 2.

Chen, G. et al., "Gradient micropattern immobilization of EGF to investigate the effect of artificial juxtacrine stimulation," Biomaterials. Sep. 2001, pp. 2453-2457, vol. 22, No. 18.

International Preliminary Report on Patentability for Intl. Pat. Appln. No. PCT/US2011/023633, mailed on Aug. 15, 2013, 10 pp.

Loo, C., et al., "Immunotargeted nanoshells for integrated cancer imaging and therapy," Nano Lett., vol. 5, No. 4, pp. 709-711 (Mar. 22, 2005).

Nakayama, Y., and Matsuda, T., "Photocurable surgical tissue adhesive glues composed of photoreactive gelatin and poly(ethylene glycol) diacrylate," Journal of Biomedical Materials, vol. 48, Issue 4, pp. 511-521 (1999).

Pan, Y., et al., "Size-Dependent Cytotoxicity of Gold Nanoparticles," Small, vol. 3, Issue 11, pp. 1941-1949 (Oct. 2007).

Pissuwan, D., et al., "Therapeutic possibilities of plasmonically heated gold nanoparticles," Trends in Biotechnology, vol. 24, No. 2, pp. 62-67 (Feb. 2006).

Troutman, T. S., et al., "Light-induced content release from plasmon-resonant liposomes," Advanced Materials, vol. 21 Issue 22, pp. 2334-2338 (Mar. 23, 2009).

Ye, L., et al., "Angiomyogenesis using liposome-based vascular endothelial growth factor-165 transfection with skeletal myoblast for cardiac repair," Biomaterials, vol. 29, Issue 18, pp. 2125-2137 (May 2008).

\* cited by examiner

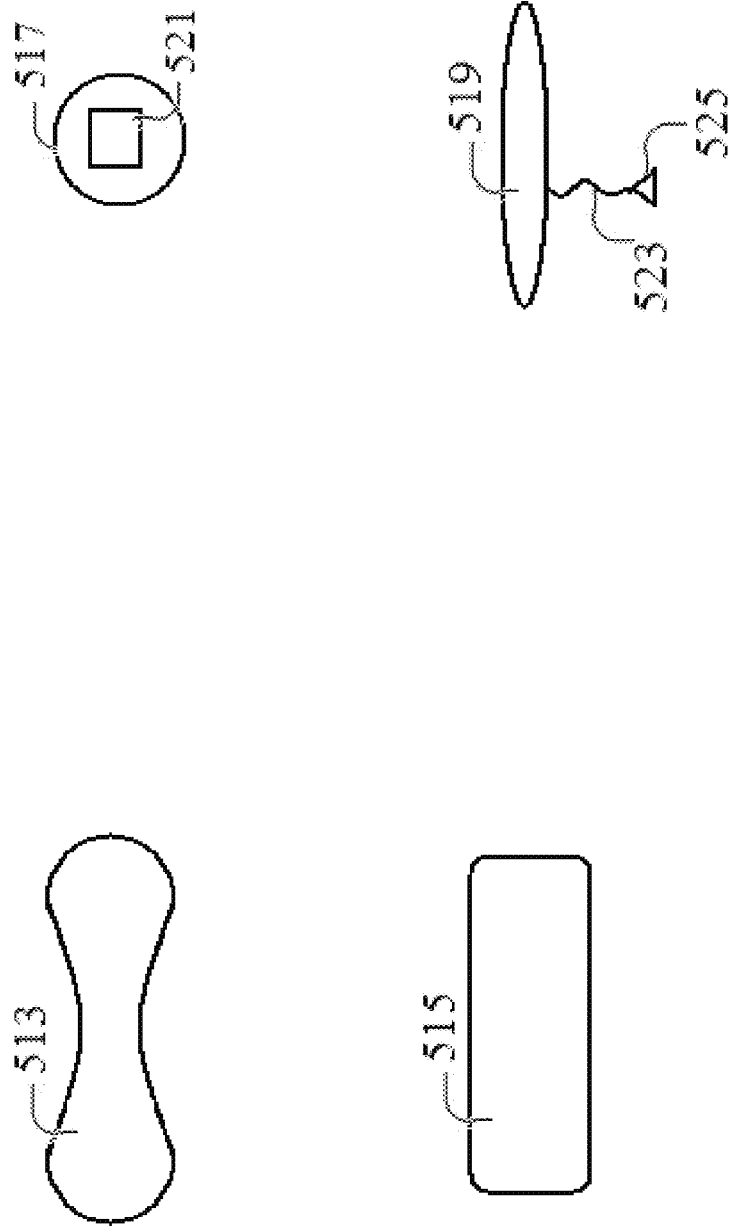

SELECTIVE 3D BIOPATTERNING

CROSS-REFERENCE TO RELATED APPLICATIONS

This application is a 35 U.S.C. §371 national phase entry of PCT/US2011/023633, filed Feb. 3, 2011, which is incorporated herein by reference in its entirety.

BACKGROUND

Current tissue engineering applications use stem cells that must differentiate into specific cell types to form tissues and organs. Controlling the broad differentiation potential of stem cells in order to generate desired cell lineages is difficult using existing methods. Stem cells are generally positioned on a scaffold and various biochemical factors are added in order to steer the differentiation of the cells into the desired lineages. Lack of access to interior regions of tissues and organs increases the difficulty of exercising control over cell differentiation and tissue construction.

BRIEF DESCRIPTION OF THE FIGURES

The presently disclosed subject matter is particularly pointed out and distinctly claimed in the concluding portion of the Specification. The foregoing and other features of the present disclosure will become more fully apparent from the following Detailed Description and appended Claims, taken in conjunction with the accompanying Figures. Understanding that these Figures depict example embodiments in accordance with the disclosure and are, therefore, not to be considered limiting of its scope, the disclosure will be described with additional specificity and detail through use of the accompanying Figures, in which:

FIGS. 5a-5e illustrate examples of patterns and photosensitive elements;

DETAILED DESCRIPTION

Figure 1:
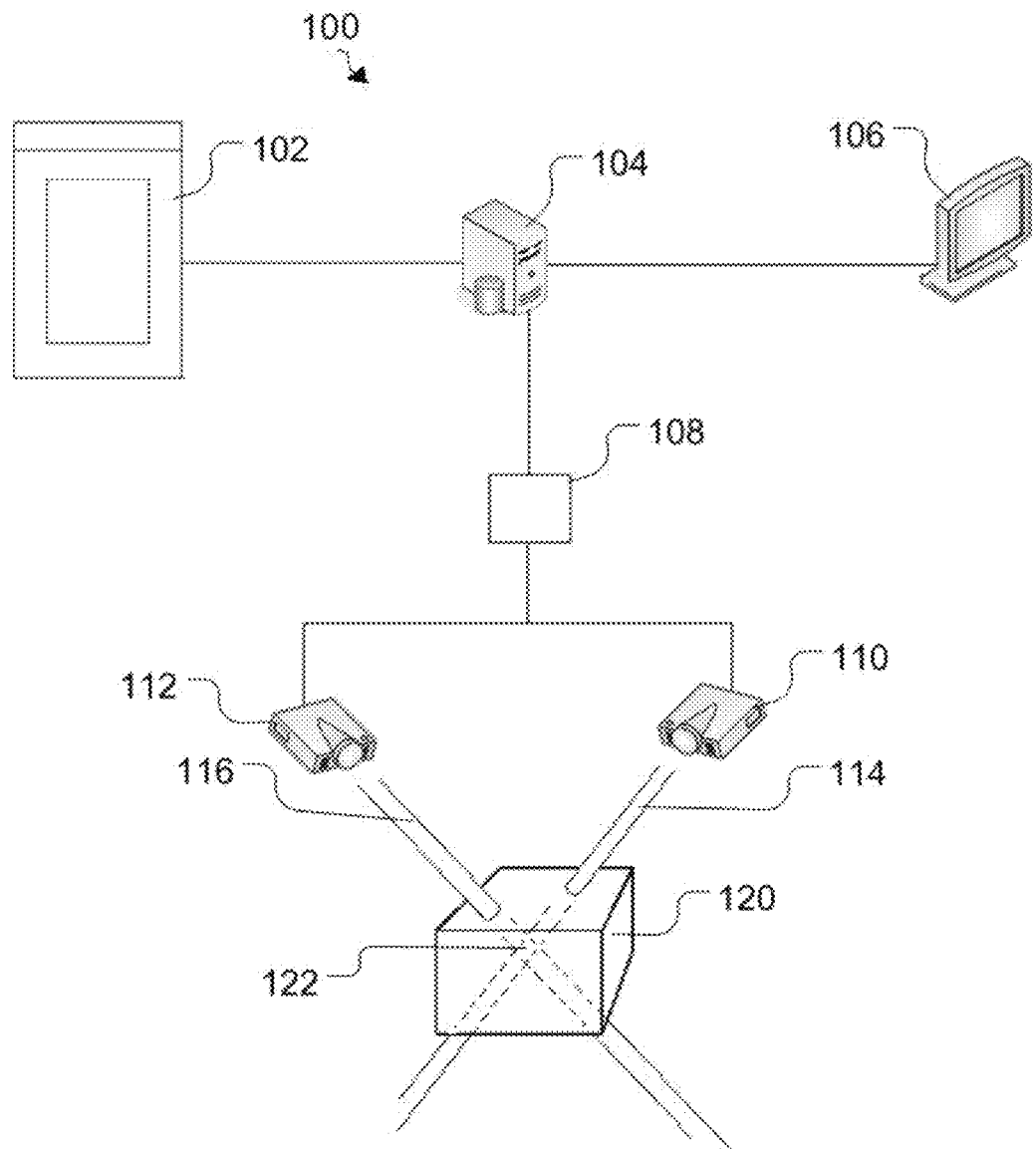
FIG. 1 illustrates a schematic diagram of a selective 3D biopatterning system.

The present Description sets forth various examples along with specific details to provide a thorough understanding of claimed subject matter. It will be understood by those skilled in the art, however, the claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following Detailed Description, reference is made to the accompanying Figures, which form a part hereof. In the Figures, similar symbols typically identify similar components, unless context dictates otherwise. The illustrative embodiments described in the present Detailed Description, Figures, and Claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

The present disclosure is drawn, inter alia, to methods, systems, and articles for selective three dimensional (3D) biopatterning. A biological target may be provided with photosensitive elements designed to be activated (e.g., become heated, vibrate, adhere to the biological target, release a biochemical factor, and/or change conformation) by electromagnetic (EM) radiation delivered at the activation wavelength and/or minimum threshold dose of the photosensitive elements. Beams of radiation having various shapes, wavelengths, intensities, and other characteristics may be emitted into the biological target to produce an intersection in a desired three-dimensional (3D) shape within a selected area of the target. The duration of emission and the number and characteristics of the beams may be determined based on factors such as the depth and shape of target area, the density/opacity of the target material, characteristics of the photosensitive elements to be activated, and the desired effect.

Within the intersection, the additive/combined energies of the beams may exceed the radiation dose delivered to surrounding areas. The radiation dose within the intersection of the beams may reach or exceed a minimum threshold dose for activation of a photosensitive element, while the radiation dose in surrounding areas exposed to fewer beams may fall below the minimum threshold. Thus, the numbers, wavelengths, intensities, duration of emission, and other characteristics of the emitted beams may be selected to differentially activate one or more groups of photosensitive elements within a 3D area of the biological target at a desired time. In various examples, beam intersections may be created in a biological target to position adhesive growth factors within an organ scaffold, to selectively delete cells during tissue growth, and/or to release biochemical factors.

The present disclosure describes methods for biopatterning a biological target. In some example methods, a radiation pattern to be applied to an area of the biological target is selected. The radiation pattern defines at least one shape. A first group of photosensitive elements is added to the biological target. The first group is responsive to a first activation wavelength. A first light is radiated into the area of the biological target in a first shape that is selected based at least partially on the selected radiation pattern. The first light includes at least the first activation wavelength. The first activation wavelength is in the range of 1 mm to 760 nm, 760 nm to 380 nm, or 380 nm to 10 nm. In some examples, the first shape is the shape of the selected radiation pattern, and the first beam of light activates at least some of the first group of photosensitive elements located in the area of the biological target. Some example methods may include selecting one or more contours of the area from an image of the biological target. Example methods may also include scanning the biological target to generate scan data and generating the image of the biological target from the scan data. In some examples, selecting the radiation pattern includes selecting the one or more contours of the area, and the radiation pattern is defined by the one or more contours. In other examples, selecting the one or more contours includes selecting a 3D area of the image, and the selected radiation pattern is a 3D pattern.

Some example methods include radiating at least a second light into the biological target in a second shape. The second light includes at least the first activation wavelength, and the second shape is based at least partially on the selected radiation pattern. The second light intersects with the first light within the area of the biological target. The intersection reproduces the at least one shape defined by the radiation pattern. A first plurality of the photosensitive elements of the first group are located within the intersection and are activated by the first and second lights. A second plurality of the photosensitive elements of the first group are not located within the intersection and are not activated.

Some example methods also include adding a second group of photosensitive elements to the scaffold. The second group has a second activation wavelength. The second activation wavelength is in the range of 1 mm to 760 nm, 760 nm to 380 nm, or 380 nm to 10 nm, and is greater than the first activation wavelength. The first and the second groups of photosensitive elements are activated to adhere to the biological target within the intersection to form a 3D structure in the area of the biological target. The first group of photosensitive elements includes one or more photo-adhesive molecules, photo-adhesive biochemical factors, or nanoparticles.

The present disclosure also describes systems for selective 3D biopatterning. Example systems may include a computing system and a radiation source. The computing system is configured to select an area within an image of a biological target, and the selected area defines a radiation pattern. The radiation source is coupled to the computing system and is configured to radiate one or more lights into the biological target. The one or more lights reproduce the defined radiation pattern in the selected area of the biological target. The radiation source may include a first radiation element and a reflector. Some example systems may include a display coupled to the computing system. The display is configured to render the image of the biological target.

An example system may include an imager coupled to the computing system. The imager is configured to scan the biological target and to send scan data of the biological target to the computing system, and the computing system is configured to generate the image of the biological target from the scan data. Some example systems include a controller coupled to the computing system and to the radiation source. The controller is configured to control the reflector. In some examples, the reflector is a digital micromirror device, and the controller is a digital micromirror controller. The light source may include a second radiation source that has a second digital micromirror device. Some examples systems include an input device configured to receive an input, and the computing system is configured to select the area within the image of the biological target based at least on the input received through the input device.

The present disclosure also describes methods for patterning tissue growth. Some example methods include adding a first group of photosensitive elements to a biological target, defining a 3D radiation pattern to be applied to a selected area of the biological target, radiating a first light into the biological target in a first shape, and radiating a second light into the biological target in a second shape. The first group of photosensitive elements is responsive to a first activation wavelength. The 3D radiation pattern defines a 3D shape. The first light includes the first activation wavelength, and the first shape is based at least partially on the defined radiation pattern. The second light also includes the first activation wavelength, and the second shape is also based at least partially on the defined radiation pattern. The first and second non-visible lights define an intersection within the selected area of the biological target. The intersection has contours corresponding to the 3D shape. A first plurality of the first group of photosensitive elements are located in the intersection and are activated by the first and second lights. A second plurality of the first group of photosensitive elements are not located in the intersection and are not activated by the first and second lights.

In some example methods, the biological target is a selected one of a tissue, an organ, or a scaffold. At least some of the photosensitive elements of the first group are coupled to one or more biochemical factors, and the photosensitive elements are configured to release the one or more biochemical factors in response to radiation of the first excitation wavelength. The biochemical factors include at least one of a growth factor, a nucleic acid molecule, a ribonucleic acid molecule, or a protein. In some examples, radiating the first and the second lights includes pulsing at least one of the first and the second lights. The photosensitive elements of the first group may include nanoparticles with an outer surface, and at least some of the nanoparticles of the first group are selectively targeted to a specific location within the biological target by a targeting molecule coupled to the outer surface.

Some example methods may also include adding a second group of photosensitive elements to the biological target. The second group of photosensitive elements is responsive to a second activation wavelength. The first activation wavelength is in the range of 1 mm to 760 nm, 760 nm to 380 nm, or 380 nm to 10 nm. The second wavelength is in the range of 1 mm to 760 nm, 760 nm to 380 nm, or 380 nm to 10 nm, and is different from the first activation wavelength.

The present disclosure also describes scaffolds configured to support tissue formation. Some example scaffolds may include a 3D structural support and one or more groups of photosensitive elements coupled to the 3D structural support. The 3D structural support is constructed of one or more biocompatible materials. The photosensitive elements are positioned within the 3D structural support in a pattern corresponding to a desired pattern of tissue formation. At least some of the photosensitive elements of the one or more groups include photo-adhesive molecules coupled to biochemical factors, and the photo-adhesive molecules are directly coupled to the 3D structural support. In some examples, at least some of the photosensitive elements of the one of the one or more groups include nanoparticles. The nanoparticles are coupled to one or more of photo-adhesive molecules or biochemical factors. In some examples, the photosensitive elements of at least a first one of the groups includes photo-adhesive molecules coupled to biochemical factors, with the photo-adhesive molecules directly coupled to the 3D structural support, and the photosensitive elements of at least a second one of the groups include nanoparticles.

The present disclosure also describes non-volatile computer readable storage mediums that include executable instructions operable, upon execution by a computing system, to define an area within an image of a biological target. The defined area has one or more outer contours and corresponds to an area of the biological target. In some examples, the executable instructions are further operable, upon execution, to select a radiation pattern to be applied to the corresponding area of the biological target. In other examples, the executable instructions further operable, upon execution, to create a radiation pattern to be applied to the corresponding area of the biological target based at least partially on an input received through an input device. The defined area may be a 3D area and the radiation pattern may be a 3D radiation pattern. The radiation pattern may be selected from among a plurality of pre-stored radiation patterns.

As used herein, the term "biopatterning" refers to the selective placement and manipulation of cells, biochemical factors, nanoparticles, and/or other factors within a biological target through the targeted application of EM radiation (e.g., non-visible light). The present disclosure is also drawn to a patterned substrate, such as a patterned 3D substrate. As used herein, the term "patterned substrate" refers to a product resulting from the biopatterning of a scaffold or other substrate. For example, a patterned substrate can be a de-celled or artificial 3D organ scaffold with photo-adhesive biochemical factors bound to the scaffold in one or more layers to form a pattern designed to direct cell growth/differentiation.

The term "radiation pattern" collectively refers to any one or more shapes, images, and/or patterns to be formed or reproduced within a biological target using EM radiation. For example, a radiation pattern may define a 3D shape, and the 3D shape may be reproduced within the biological target by emitting two or more beams of light along intersecting vertices into the biological target such that the outer contours of the intersection(s) reproduces the outer contours of the shape(s). A radiation pattern may include any number of 2D and/or 3D shapes in any combination, and may be reproduced in a biological target using any number of beams of EM radiation (e.g., beams of UV, IR, and/or visible light).

As used herein, a "photosensitive element" can be any molecule and/or object that changes shape or conformation, becomes heated, adheres to another substance, participates in a chemical reaction, and/or displays an excitation behavior (e.g., vibration/resonance) upon exposure to EM radiation. The term "activation" and derivatives thereof are used herein to indicate any one or more of these responses. A photosensitive element may be responsive to a specific wavelength, or specific range of wavelengths, of EM radiation. The term "activation wavelength" collectively refers to the wavelength or range of wavelengths to which a photosensitive element is responsive (i.e., that trigger activation).

In some examples, activation of a photosensitive element may occur as a result of exposure to EM radiation at the activation wavelength once a minimum threshold dose is reached. A "minimum threshold dose" is the lowest dose of EM radiation (at the activation wavelength) that causes the activation of a photosensitive element. Photosensitive elements exposed to a radiation dose below the minimum threshold may exhibit some level of response that is less than "activation." For example, the activation of a photosensitive element within a beam intersection may result in the adhesion of the photosensitive element to the biological target. A similar photosensitive element that is outside the beam intersection but is exposed to a dose of radiation below the minimum threshold level may become adhesive to a lesser degree than the "activated" photosensitive element, and may be washed away by a controlled washing or rinsing step while the activated photosensitive element remains bound to the biological target.

The term "photo-adhesive" is used to refer to a photosensitive element (or a component thereof) that is designed to adhere to a substrate upon exposure to EM radiation of an activation wavelength. A photosensitive element that is photo-adhesive may adhere to a substrate as a result of electron movement triggered by photons (i.e., EM radiation delivered at the activation wavelength). In some examples, a photosensitive element can include a photo-adhesive molecule coupled to a biochemical factor and/or nanoparticle.

The term "photo-reactive" is used to refer to a photosensitive element (or a component thereof) that is designed to change conformation, become heated, participate in a chemical reaction, and/or display an excitation behavior (e.g., vibration/resonance) in response to EM radiation of an activation wavelength. A photosensitive element that is photo-reactive can be, or include, a nanoparticle.

A photosensitive element may have one, two, three, or more than three components. A photosensitive element can include, for example, a nanoparticle, a biochemical factor, a biochemical factor derivative, a targeting molecule, and/or a photo-adhesive molecule. A photosensitive element can have two or more components responsive to different activation wavelengths and/or minimum threshold doses, allowing the photosensitive element to be activated more than once for different purposes. Examples of photosensitive elements include, but are not limited to, a photo-adhesive molecule coupled to a biochemical factor, a photo-adhesive molecule coupled to a nanoparticle, a nanoparticle coupled to a biochemical factor, and a nanoparticle coupled to a biochemical factor and to a photo-adhesive molecule. Some photosensitive elements may be both photo-adhesive and photo-reactive.

As used herein, a "biochemical factor" can be or include any peptide, glycoprotein, protein, steroid, lipid, carbohydrate, nucleic acid, ribonucleic acid and/or other molecule that affects the growth, differentiation, proliferation, metabolism, attachment, migration, secretory activity, and/or other function of a viable cell. Examples of biochemical factors include but are not limited to growth factors, cytokines, chemokines, hormones, interleukins, and extracellular matrix components. The term "biochemical factor" also encompasses derivatives of the above molecules, such as truncated or otherwise modified forms of biochemical factors that retain one or more of the above functions.

As used herein, a "nanoparticle" is a particle that measures no more than 300 nm in at least one dimension and is responsive to (i.e., can be activated by) EM radiation of an activation wavelength. Activation of the nanoparticle may cause the nanoparticle to heat, vibrate, change conformation, and/or release a biochemical factor. Nanoparticles may vary in composition, shape, and dimensions. Groups of nanoparticles with different activation wavelengths may be used in a biological target to allow selective activation of different nanoparticles in the same area of the biological target. Activated nanoparticles may change conformation to release a surface-bound or enclosed biochemical factor and/or may cause the arrest or deletion of cells (e.g., during construction of tissues or organs). The term "arrest" refers to the induction of a state of slowed or halted cell growth, metabolism, and/or proliferation. The term "deletion" refers to the induction of necrosis, apoptosis, non-apoptotic programmed cell death, anoikis, autophagic cell death, and/or any other type of cell death. Arrest/deletion may occur as a result of heating or mechanical disruption of a cell or some part thereof, absorption of EM radiation, and/or scattering of EM radiation.

A nanoparticle can have a core and one or more outer layers constructed of any one or more of gold, silica, carbon, calcium phosphate, iron oxide, magnetite, a polymer, or other biocompatible material, alone or in any combination. For example, a nanoparticle can have a silicon core and one or more outer layers of gold. Nanoparticles can be provided in one or more shapes, such as but not limited to spherical, semi-spherical, horn-shaped, tubular or rod-shaped, elongate with enlarged ends, etc.

Alternatively, a nanoparticle can be a porous or non-porous hollow shell (e.g., a hollow gold nanosphere, a carbon nanotube, a carbonaceous capsule, a calcium phosphate nanoshell, etc.) designed to enclose a biochemical factor and to release the enclosed biochemical factor in response to exposure to EM radiation. The enclosed biochemical factor may be attached to an interior surface of the hollow shell. Alternatively, the biochemical factor may be enclosed within the hollow shell but not coupled to the interior surface of the hollow shell. Again, release of the enclosed biochemical factor may occur due to melting, conformational change, or degradation of the nanoparticle induced by exposure to EM radiation of the activation wavelength. Hollow nanoparticles designed to enclose one or more substances may be prepared using known methods, including but not limited to the methods described by Altinoglu et al., "Near-Infrared Emitting Fluorophore-Doped Calcium Phosphate Nanoparticles for In Vivo Imaging of Human Breast Cancer," *ACS Nano* 2:2075-2084 (2008); Cai et al., "Ultrasound Controlled Morphology Transformation of Hollow Calcium Phosphate Nanospheres: A Smart and Biocompatible Drug Release System," *Chem. Mater.* 19:3081-3083 (2007); You et al., "Exceptionally High Payload of Doxorubicin in Hollow Gold Nanospheres for Near-infrared Light-triggered Drug Release," *ACS Nano* 4(2):1033-1041 (2010); Son et al., "Inorganic Hollow Nanoparticles and Nanotubes in Nanomedicine Part 1. Drug/gene Delivery Applications," *Drug Disc. Today* 12(15/16):650-656 (2007). These disclosures are incorporated by reference herein.

A nanoparticle can be coupled along an outer surface to a biochemical factor. The biochemical factor may be released from the nanoparticle upon exposure of the nanoparticle to EM radiation of the activation wavelength. This may occur due to melting, a conformational change, or degradation of the nanoparticle. Methods for preparing nanoparticles are known in the art, and include but are not limited to the methods described by Chen et al., "DNA-gold Nanorod Conjugates for Remote Control of Localized Gene Expression by Near Infrared Radiation," *J. Am. Chem. Soc.* 128:3709-3715 (2006); Wijaya et al., "Selective Release of Multiple DNA Oligonucleotides from Gold Nanorods," *ACS Nano* 3(1):80-86 (2009); Loo et al., "Nanoshell-enabled Photonics-based Imaging and Therapy of Cancer," *Tech. in Cancer Res. & Treat.* 3(1):33-40 (2004). These disclosures are incorporated by reference herein.

A nanoparticle can be coupled along its outer surface to one or more stabilizing, solubility-enhancing, and/or hydrophilic molecules. For example, a nanoparticle may have a multivalent or polymeric coating that includes polar molecules such as (but not limited to) polyethylene glycol. A nanoparticle may also/instead be coupled to one or more targeting molecules, which may include a biochemical factor, for directing the nanoparticles to a particular cell type, tissue type, or to a particular location within a cell, scaffold, tissue, organ, or other biological target. Examples of targeting molecules include but are not limited to antibodies, nucleic acids, aptamers, streptavidin, and peptides. A targeting molecule may be covalently linked to an outer surface of the nanoparticle. Alternatively, a targeting molecule may be coupled to another component of a photosensitive element, such as a biochemical factor.

In some examples, photosensitive elements may be provided in a biological target such as a scaffold. A "scaffold" can be any material and/or three-dimensional structure capable of providing an attachment site for cells. A scaffold may be derived from a tissue or organ and/or constructed de novo. A scaffold can include collagen and/or other connective biological tissues, a polymer, a hydrogel, and/or a synthetic or semi-synthetic material. A scaffold can be a 3D substrate, such as a donor or synthetic organ (e.g., a heart, kidney, bladder, eye, etc.) with cellular material removed. Methods for the removal of cells from an organ are described, for example, by Ott et al., "Perfusion-decellularized Matrix: Using Nature's Platform to Engineer a Bioartificial Heart," *Nature Med.* 14:213-221 (2008) and Taylor et al., U.S. Patent Application Pub. No. 2010/0093066, which are incorporated by reference herein.

A scaffold may be at least partially constructed of a substrate that is substantially radiotransparent, such as one or more polymers, gels, or other substances that are partially or fully transparent to infrared, visible, and/or ultraviolet radiation. A scaffold may include a ceramic substrate that is substantially transparent to ultraviolet, visible, and/or infrared radiation. An example of a suitable transparent ceramic substrate is described by John et al., "In vitro Investigations of Bone Remodeling on a Transparent Hydroxyapatite Ceramic," *Biomed. Materials* 4(1):015007 (2009), hereby incorporated by reference.

Other scaffolds may be artificially created matrices including one or more biomaterials such as, but not limited to, polylactic acid, polyglycolic acid, polycaprolactone, polyesters, glycosaminoglycans, hyaluronic acid, collagen, silicone, and other biocompatible materials. Scaffolds may be constructed using any known method, including but not limited to ink jet printing of polymer powders and/or fuse deposition modeling of a polymer melt.

In various aspects, photosensitive elements within a scaffold or other biological target may be selectively activated by emitting one or more beams of light into the biological target. The beams may intersect within a selected area of the biological target to create a desired 2D or 3D shape defined by the intersection(s). The number and shapes of the beams may be selected to produce an intersection in any desired shape within the biological target. The wavelengths, intensity, and duration of emission of each beam may be selected based at least in part on the characteristics of the photosensitive elements targeted (e.g., activation wavelength) and/or minimum threshold dose and the scaffold (density/opacity, depth). This may allow selective activation of only those photosensitive elements that are within the intersection and are responsive to the emitted wavelength(s).

In one aspect, photosensitive elements may have a photoadhesive component that is designed to adhere to a biological target, such as a scaffold, upon exposure to EM radiation of an activation wavelength. The photosensitive elements may be applied to the scaffold by immersing the scaffold in a solution containing the photosensitive elements, spraying a solution of the photosensitive elements onto the scaffold, or other known methods. The photosensitive elements may be selectively activated using one or more beams of light as described above. Portions of the scaffold that are not within the intersection may receive a lower radiation dose that falls below a minimum threshold dose for activation of the photosensitive elements. The photosensitive elements in those portions of the scaffold may be subsequently removed by rinsing them from the scaffold.

The addition of photosensitive elements to a biological target, selective activation, and subsequent removal of unbound photosensitive elements may be repeated to create one or more biopatterns within the biological target. Photosensitive elements that are photo-adhesive may be adhered to a scaffold any number of times in successive layers to create a biopattern with a complex 3D structure.

When cells are added to the scaffold, the photosensitive elements may influence growth, migration, differentiation, and other cellular processes in accordance with the created biopattern. For example, a biochemical factor such as heparin may be coupled with a photo-adhesive molecule such as azidoaniline to produce photo-sensitive heparin that adheres to the scaffold or other substrate upon exposure to UV radiation at wavelengths within the range of 260-280 nm (see e.g., Park and Ito, "Micropattern-immobilization of Heparin to Regulate Cell Growth with Fibroblast Growth Factor," *Cytotechnology* 33(1):117-122 (2000), incorporated by reference herein). In another example, photosensitive elements may be immobilized in a pattern along an interior surface of a hollow 3D scaffold to enhance the adhesion, growth, and/or differentiation of cells along that surface.

In another aspect, photosensitive elements may be photo-reactive and not photo-adhesive. For example, a photosensitive element may be (or may include) a nanoparticle. Photosensitive elements that are not photo-adhesive may be placed within cells by known methods including but not limited to injection, gas gun injection, electroporation, endocytosis, or viral vector. For example, the photosensitive elements may be placed within cells by gas gun injection and the cells may be subsequently added to a scaffold to form a tissue. Alternatively, photosensitive elements may be placed within cells in situ (e.g., in a tissue, organ, on in/on a scaffold) by gas gun injection or with a viral vector. In some examples, photosensitive elements may be added to cells, tissue, and/or a scaffold by rinsing or by any of the above methods. The photosensitive elements may bind to one or more exterior surfaces of the cell, tissue, or scaffold. Such photosensitive elements may include, for example, an antibody, a lectin, or another molecule that adheres to the exterior surface of the cell, tissue, or scaffold.

The photosensitive elements may be selectively activated within the cells using EM radiation as described above. In one example, the photosensitive elements may be added to cells in cell culture medium and may enter the cells by way of endocytosis. The cells may be added to a scaffold (e.g., a biopatterned scaffold) and may proliferate to form a tissue. EM radiation may be used to activate the photosensitive elements during or after tissue formation in order to induce heating, vibration, and/or release of a biochemical factor within cells in one or more areas of the tissue.

In some aspects, photosensitive elements may have a photo-adhesive molecule coupled to a photo-reactive nanoparticle. The photo-adhesive molecule may have a first activation wavelength and the photo-reactive nanoparticle may have a different (second) activation wavelength. The photosensitive elements may be selectively adhered to a scaffold by directing EM radiation of the first activation wavelength into the scaffold as described above, resulting in the anchoring of the photosensitive element to the scaffold. The photo-reactive nanoparticle portion of the photosensitive element may be selectively activated in situ using EM radiation of the second activation wavelength.

Activation of the photosensitive element with EM radiation of the second activation wavelength may cause localized heating/vibration and/or release of a biochemical factor. In some examples, the photo-reactive nanoparticle portion of the photosensitive element may be exposed to EM radiation of the second wavelength until a first minimum threshold dose has been delivered, resulting in the release of an enclosed or surface-bound biochemical factor. The photo-reactive nanoparticle portion may be activated again using EM radiation of the second wavelength but at an increased intensity or for an increased duration to deliver a second minimum threshold dose. This second activation may cause increased localized heating sufficient to cause arrest or death of a cell.

Photosensitive elements may be selected or designed for use in biopatterning applications based on desired effect, location of use, tissue type, and other factors. For example, photosensitive elements may be selected for biopatterning areas within solid tissues based at least in part on the radiation wavelength required for the relevant depth of tissue penetration. Longer wavelength radiation may penetrate more deeply into biological tissues than shorter wavelength radiation. Thus, a photosensitive element with an activation wavelength in the range of 10 nm to 400 nm (i.e., UV range) may be selected or designed for biopatterning applications requiring relatively shallow penetration of a scaffold, tissue, or other target. Such photosensitive elements may be, or may include, a photo-adhesive molecule with an activation wavelength in this range (e.g., photosensitive heparin, described above). The photo-adhesive molecule may be coupled to a biochemical factor and/or to a nanoparticle. Examples of photosensitive elements with an activation wavelength in the UV range are provided throughout the specification and figures (see e.g., FIGS. 5a, 5b, and the accompanying description below). In contrast, a photosensitive element with an activation wavelength in the range of 700 nm to 2 μm (i.e., IR range) may be selected or designed for biopatterning applications requiring a greater depth of tissue penetration. Such photosensitive elements may be, or may include, a photo-reactive nanoparticle (e.g., a gold nanosphere) with an activation wavelength in this range. The photo-reactive nanoparticle may be coupled to a biochemical factor and/or to a photo-adhesive molecule. Examples of photosensitive elements with an activation wavelength in the IR range are provided throughout the specification and figures (see e.g., FIGS. 5c-5e, and the accompanying description below).

Similarly, the wavelength(s) of the beam(s) may be selected or calculated based at least in part on the activation wavelength(s) of the photosensitive elements targeted for activation. Wavelengths may also be selected or calculated based at least in part on the desired radiation dose to be applied within the selected area of the target, number of beams, angles of the beams relative to the target and/or to one another, predicted beam interactions and combined/cumulative beam energies, target density, and any other factors relevant for delivering the desired radiation dose. Beams of radiation may be applied at any suitable wavelength, including but not limited to wavelengths within the ranges of 1 mm to 700 nm (infrared), 700 nm to 400 nm (visible), or 400 nm to 10 nm (ultraviolet).

The radiation dose, duration of radiation exposure, and radiation source power may be adjusted in accordance with various characteristics of the biological target, the beams, photosensitive elements, and other factors. Radiation dose (D) is approximately equal to the product of dose intensity (I) and duration of exposure (T): $D=I \times T$. The intensity (I) is the sum of the intensities of the intersecting beams (e.g., $B_{1i} + B_{2i} = I$). The intensity of an individual beam ($B_i$) can be calculated by dividing beam energy ($B_e$) by the cross-sectional area irradiated (A). The duration of exposure may be within the ranges of 0.1-1.0 second, 1-20 seconds, 10-30 seconds, 20-60 seconds, 30 seconds to 2 minutes, 1-5 minutes, or 1-30 minutes. Radiation sources used may be in the ranges of 0.5-5 watts, 1-10 watts, 5-50 watts, 10-100 watts, or 100-1000 watts. For example, the intensity of a 125 mW beam over a cross-sectional surface area of 1 $cm^2$ is 125 $mW/cm^2$, and the radiation dose received by a section of a scaffold irradiated for 200 seconds with two such UV light beams would be 500 $mJ/cm^2$. The minimum threshold dose of a photosensitive element may be determined experimentally, retrieved from an information source such as a database, or determined/estimated based on one or more characteristics of the photosensitive element (e.g., size, composition, activation wavelength).

The number of beams may be selected based at least in part on the desired difference in radiation dose between the beam intersection and the remaining areas of the biological target. The difference between the radiation dose within the beam intersection and the radiation dose in other areas may be increased by using more beams at lower intensities to create the beam intersection. Alternatively, the difference may be increased by emitting the beams in shorter pulses and repositioning the beams periodically such that the beams do not pass through the same non-targeted areas of the tissue each time the beams are emitted.

A selective 3D biopatterning system as described herein may be used to selectively apply radiation within the contours of a 3D area of a biological target to cause adhesion or activation of a photosensitive element. In previously described systems, a "pattern mask" is used to prevent exposure of one or more portions of the target to the radiation. The pattern mask is constructed by cutting or removing material from a solid plate of a material designed to block EM radiation. The pattern mask is then placed over the surface of the substrate to be irradiated and a radiation source is directed indiscriminately to the entire surface. The pattern mask allows the radiation to reach only the portions of the substrate surface corresponding to the cut pattern of the plate, resulting in the adhesion of photosensitive elements on a one-dimensional surface according to the pattern cut from the plate. An example of such a system is described by Park and Ito (2000).

In contrast, a selective 3D biopatterning system as described herein provides selective patterning of three-dimensional target areas without the use of a pattern mask. FIG. 1 illustrates a schematic diagram of an embodiment of a selective 3D biopatterning system 100 arranged in accordance with various embodiments. System 100 may be used to apply EM radiation within the outer contours of a selected area of a 3D biological target 120 (e.g., a scaffold, a tissue, an organ, a body) according to a radiation pattern. As illustrated, system 100 may include computing system 104 operatively coupled to imager 102, display 106, controller 108, and radiation sources 110 and 112. Radiation sources 110 and/or 112 may be repositionable to direct one or more beams of light 114/116 toward biological target 120. An intersection 122 may be created on or within biological target 120 where beams of light 114 and 116 intersect.

Although FIG. 1 illustrates two radiation sources 110 and 112, it is apparent to those skilled in the art that the number and location of the radiation sources can be various depending on a shape, size, or number of radiation patterns to be created. In some examples, radiation sources 110 and 112 may be a single device that emits two, three, or more beams of radiation. In other examples, one, two, three, or more radiation sources may be disposed in fixed locations and may emit radiation from some or all of those locations in a selectable manner. Some selective 3D biopatterning systems may lack controller 108. In those systems, one or more other system components (e.g., computing system 104, radiation sources 110/112, and/or imager 102) may be configured to perform some or all of the functions of controller 108. The illustrated components of system 100 are merely one example, and any of the components may be combined and/or may perform some or all of the functions ascribed to any other component. In another example, controller 108, computing system 104, and imager 102 may be integrated within a single device.

Imager 102 can include any imaging device configured to create a representative image of a biological target. Imager 102 can include, for example, a scanner, a radiography (e.g., X-ray) imaging device, a tomography imaging device, a magnetic resonance imaging device, a nuclear magnetic resonance imaging device, a photoacoustic/optoacoustic imaging device, a thermography imaging device, an ultrasound imaging device, and/or any combination thereof. Imager 102 may further include a processor and/or logic for producing 2D and/or 3D images from image data.

Figure 7:
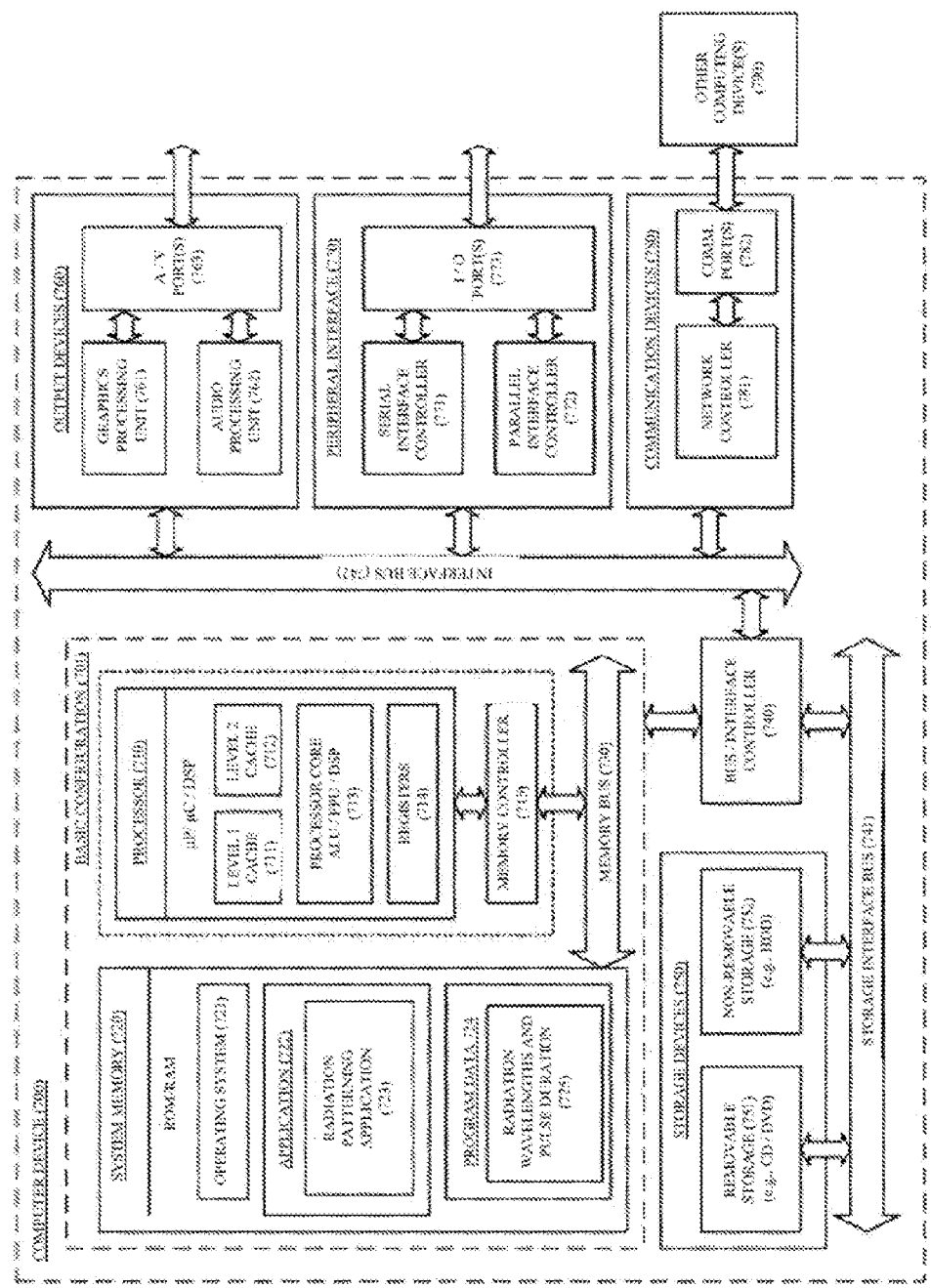
FIG. 7 is a block diagram illustrating an example computing device, all arranged in accordance with at least some embodiments of the present disclosure.

Computing system 104 can include a personal computer, a laptop computer, a portable computer, a tablet computer, a mobile device, or other programmable machine. Computing system 104 may be embedded within another system device or component, such as imager 102 or radiation source 110/112. An example of computing system 104 is illustrated in FIG. 7.

Display 106 can include, but is not limited to, a monitor and/or 3D display (e.g., stereoscopic, autostereoscopic, holographic, volumetric, free-space display, etc.) device. For example, display 106 may be a touch-screen. Display 106 may communicate with a pointer, a stylus, and/or other input device for selection of a 3D area within an image. In one example, display 106 may be a 3D display configured to project an image and facilitate selection of a 3D area of the image through interaction of a user with the projected image. Imager 102, computing system 104, and/or display 106 may be integrated within a single device. Alternatively, imager 102 may be a remote device in wired or wireless communication with computing system 104 and/or display 106.

Radiation source 110/112 may be configured to project, reflect or otherwise emit radiation patterns into a biological target. Radiation source 110/112 can include any device configured to emit visible light, ultraviolet (UV) radiation, infrared (IR) radiation, radio waves, X-rays, and/or any other type of EM radiation. For example, radiation source 110 and/or radiation source 112 can include one, two, three or more micromirror matrices and/or digital micromirror devices. Digital micromirror devices (DMD), such as the Texas Instruments Digital Micromirror Device, and examples of DMD applications are further described in Dudley et al., "Emerging Digital Micromirror Device (DMD) Applications," *Proceedings—SPIE The International Society For Optical Engineering* 4985:14-25 (2003), the content of which is hereby incorporated by reference.

Radiation source 110/112 may be a DMD that projects IR or UV light images, such a conventional DMD projector from which the interior IR filter has been removed. Radiation source 110/112 or other device may also be used to project a visible light image (i.e., a fiducial image) for use as a standard of reference for measurement, calculation, and/or targeting of the beams. For example, an operator may use such a fiducial image as a guide for positioning or repositioning the biological target and/or radiations source 110/112 to ensure that the intersection of the beams is formed within the desired area of the biological target. In other examples, emission or projection of visual light from radiation source 110/112 may be blocked. A DMD (or other emission/projection devices with high frame rates) may be used to emit EM radiation into moving and/or living tissue.

Alternatively, radiation source 110 and/or radiation source 112 may be another type of projection device, such as a LCD projector. A selective 3D biopatterning system may include one, two, three, four or more radiation sources in any combination. In one example, one or more radiation sources may reflect/project two or more different types of radiation, such as near infrared (NIR) and UV. Radiation source(s) 110/112 may project or emit light into a biological target at any suitable wavelength, including but not limited to wavelengths within the ranges of 1 mm to 760 nm (infrared), 760 nm to 380 nm (visible), or 380 nm to 10 nm (ultraviolet).

Controller 108 may be coupled to computing system 104 and/or radiation sources 110/112. Controller 108 may be configured to convert data into images and/or to control frame rate, intensity, data load, and/or micromirror reset. Controller 108 may be a controller board integrated within computing system 104, radiation sources 110/112, display 106, or imager 102. In one example, radiation source 110 and/or 112 includes a digital micromirror device, and controller 108 is a DMD controller. Any one or more of computing system 104, controller 108, display 106, or imager 102 may be configured to control the location, angle, and/or position of one or more components of radiation sources 110/112. Similarly, any one or more of computing system 104, controller 108, radiation sources 110/112, display 106, or imager 102 may be configured to control the energy, shape, duration, angle, origin, and/or wavelength of a beam emitted by radiation sources 110/112.

In operation, biological target 120 may be imaged with imager 102 using known techniques. Imager 102 may communicate image data to computing system 104, and computing system 104 may process the image data. Computing system may cause an image corresponding to the image data to be rendered on/by display 106. The image may be used to select or create a radiation pattern, and computing system 104 and/or controller 108 may determine one or more parameters for the emission of EM radiation into the target (e.g., beam shape, beam angle, number of beams) based at least in part on the selected or created radiation pattern.

A 3D area within the image of biological target 120 may be selected and defined manually or automatically using computing system 104 and/or display 106. For example, a 3D area within the displayed image may be defined by using a mouse, touch screen, or other input device to create one or more contours of a desired radiation pattern (e.g., the outer contours of a star shape). The created radiation pattern may be stored by computing system 104. Alternatively, computing system 104 may be provided with software designed to recognize structural features (e.g., a vessel, a valve, a topographical feature, etc.) and to automatically select or create a radiation pattern with contours matching one or more contours of the recognized feature. Optionally, in response to a selection or creation of the desired radiation pattern, computing system 104 (see e.g. computing system 700, below) may generate an image corresponding to the selected radiation pattern.

Computing system 104 may be provided with one or more images or radiation patterns, which may be pre-stored in an integrated or removable memory (e.g. a disc/disk, a flash drive, a removable drive, a hard drive, etc.). Alternatively, computing system 104 may receive or retrieve an image or radiation pattern from a server, from another component of system 100 (e.g., the display, the imager, etc.), or from another input source. Thus, a 3D biopatterning system may lack an imaging device or may be operated without an imaging device. For example, computing system 104 may use a polyhedral 3D modeling algorithm or other 3D reconstruction algorithm (e.g., a shape-from-silhouette reconstruction algorithm) to generate a 3D model of the biological target based on stored or retrieved images of the target. Computing system 104 may then select one or more pre-stored radiation patterns based at least in part on the generated 3D model. In other examples, a pre-stored radiation pattern may be selected without imaging the biological target or constructing an image of the biological target.

Optionally, computing system 104 may generate a combined image showing the selected/received radiation pattern superimposed over an image of the biological target. The combined image may be displayed to provide visual confirmation of the selected area and radiation pattern. The superimposed image may also be provided in an interactive manner that allows automatic or manual adjustment to contours of the selected radiation pattern and/or the position of the selected radiation pattern within the biological target. For example, computing system 104 may be provided with software designed to automatically adjust the contours or position of a radiation pattern in conformity with an automatically recognized feature. In another example, the combined image may be displayed on a touch-screen display with an interface configured to allow the position/contours of the radiation pattern to be manually adjusted by an operator of the system. In still other examples, a received/retrieved radiation pattern may be used to direct radiation emission into the biological target without the creation of images by computing system 104 or other system components.

Selected or pre-stored radiation patterns can be of any suitable size, shape, and volume (e.g., 2D or 3D), and may be reproduced within a target using one beam (a 2D radiation pattern) or more than one beam (a 2D or 3D radiation pattern). Examples of radiation patterns include evenly-spaced rows of dots, squares, or other shapes, a checkerboard or grid pattern, a continuous path, a polygon having any number of sides, a sphere, a cube, etc. A radiation pattern of evenly-spaced discontinuous dots may be used for applications such as positioning photo-adhesive biochemical factors throughout a scaffold to provide anchorage sites for cells that are intended to grow to confluence within the scaffold. The same radiation pattern may be used to activate nanoparticles within a layer of tissue in order to reduce tissue thickness or encourage the growth of new tissue (e.g., by causing arrest/deletion of dispersed cells). As another example, a radiation pattern that is a continuous path may be used for positioning photo-adhesive factors along the exterior of a portion of the scaffold that corresponds to a blood vessel. A series of non-continuous radiation patterns may be used for positioning photosensitive elements in consecutive layers within a scaffold to construct 3D structures from bottom to top, side to side, etc. Random radiation patterns may be used for applying repeated pulses of radiation within a defined area of the target. This may be done, for example, to activate only a fraction of the nanoparticles at a time within the defined area. An irregularly-shaped or polygon radiation pattern may be used for the selective activation of nanoparticles in an area of abnormal cellular growth (e.g., a tumor) within a solid target tissue, organ, or body.

Computing system 104 may be configured to receive an input of data, such as through an input device (e.g., a keyboard, mouse, memory, etc.), relevant to the determination of the beam characteristics and other parameters required for producing a beam intersection within the biological target with the desired shape and for activating photosensitive elements within the intersection. The input data may include, but are not limited to, an activation wavelength and/or a minimum threshold dose for a group of photosensitive elements to be activated, one or more physical characteristics of the biological target (e.g., density, thickness, tissue type, a path loss range, etc.), and type of biological target (e.g., a scaffold, a tissue, a body). Computing system 104 may determine, based at least in part on the input data, one or more parameters such as the number and shapes of beams, beam angles, intensity, and duration of exposure.

Alternatively, computing system 104 may have one or more algorithms for determining at least some of these factors based on other input data, data received from the imager or other source, or from a pre-stored radiation pattern.

For example, computing system 104 may estimate a path loss to the selected area of the biological target based on input data such as the depth to be reached within the biological target, the opacity of the biological target, and/or an expected range of loss per unit of distance for the emitted wavelength (e.g., range of loss within 0.5-10 dB per cm of tissue for NIR wavelengths). As another example, radiation source 110/112 may emit beams of IR light into one side of the biological target and measure the IR light exiting the opposite side. Radiation source 110/112 may send the measurement data to computing system 104, and computing system 104 may use the data to estimate the path loss. Computing system 104 may then determine parameters such as beam brightness or duration of exposure based on the estimated path loss. Alternatively, a biological target may be provided with one or more identifiers, such as barcode, number, or RFID tag, coupled to the biological target or its packaging. Computing system 104 may access a local or remote source, such as database, to retrieve data associated with the biological target. Computing system 104 may then determine or adjust beam characteristics, duration of exposure, and other parameters based at least in part on the retrieved data.

Computing system 104 may be endowed with one or more algorithms for the calculation of various parameters (e.g., number of beams, shapes, wavelengths, duration of emission, intensity, directions/angles of emission or projection, etc.) required to produce a beam intersection in the selected area(s) of the biological target according to the radiation pattern. The determined factors may be communicated by computing system 104 to controller 108 and/or to radiation source 110 and/or 112 to guide the emission of EM radiation into the biological target. For example, computing system 104 may send commands to radiation source 110/112 to reproduce a simple cuboidal intersection shape by projecting two square beams of non-visible light horizontally through a biological target to intersect at a 90 degree angle. More complex or irregular shapes can be created by altering the shape of the beams and/or emitting additional beams through the tissue along intersecting vertices.

The emitted beams may intersect within the selected area of the biological target, and the outer contours of the intersection (e.g., intersection 122) may match the outer contours of the selected 3D area and/or radiation pattern. Each beam may include EM radiation of one or more wavelengths corresponding to one or more activation wavelengths of the photosensitive elements to be activated. Within the intersection, the combined energies of the beams may deliver a greater radiation dose than in the surrounding areas. The additive/combined radiation dose delivered by the emitted beams in the activation wavelength(s) within the intersection may equal or exceed a minimum threshold dose for activation of the photosensitive elements. Other photosensitive elements that are outside of the beam intersection, are not responsive to the exposure wavelengths, or are insufficiently responsive to the exposure wavelengths and/or received dose may not be activated.

Multiple groups of photosensitive elements may be provided within biological target 120. Each group may be responsive to a different activation wavelength and/or have a different minimum dose threshold. Some groups may have the same activation wavelength and/or minimum dose threshold. The different groups of photosensitive elements may be selectively activated within the biological target at desired locations and times. More than one group of photosensitive elements may be activated concurrently within the same beam intersection. Likewise, more than one group of photosensitive elements may be concurrently activated in separate areas of the biological target and/or at separate times.

For example, a first group of photosensitive elements may be gold nanospheres with a solid core and a first activation wavelength. A second group of photosensitive elements may be gold nanospheres with a hollow core enclosing a chemokine, and may have a second activation wavelength. The photosensitive elements of both groups may be within the same areas of the biological target. If the photosensitive elements of both groups are the same size and/or have the same activation wavelengths, they may be activated concurrently within the same intersection. However, even if they are of different sizes and/or are responsive to different activation wavelengths (see e.g., FIG. 5c), they may still be activated concurrently within the same intersection by providing both activation wavelengths within the beam(s). The photosensitive elements of one group may be selectively activated within the beam intersection by supplying the activation wavelength of that group, but not of the other group, in the emitted beams.

Three or more beams may be used to create two or more beam intersections simultaneously within the biological target. The activation wavelength of only the first group may be provided in the first intersection, and the activation wavelength of only the second group may be provided in the second intersection, allowing selective activation of both groups in different areas at the same time. While the example of three beams and two intersections is provided as an illustrative example, additional beams carrying any desired combination of wavelength(s) may be used to reproduce more complex shapes/structures according to a radiation pattern that provides multiple intersections.

In one example of a 3D biopatterning system, a computer 104 retrieves a pre-stored radiation pattern from a removable storage. Computer 104 receives, through a keyboard, an input of a minimum excitation threshold for a group of photosensitive nanoparticles and a selection of a target type (e.g., "de-celled heart scaffold"). Based on the pre-stored radiation pattern and the input, computer 104 determines the number of beams, shapes, wavelengths, duration, projection angles, and other data required to guide EM radiation emission. Computer 104 communicates these data to controller 108, which is coupled to a digital micromirror array and radiation source 110/112. Controller 108 controls the emission of EM radiation from radiation source 110/112 and the repositioning of individual micromirrors within the array, causing the array to reflect beams of EM radiation that include the activation wavelengths and intersect within the target. The beams are reflected at the appropriate angles and locations to produce a beam intersection within the selected area of the biological target, with the contours of the intersection matching those of the selected area. The radiation dose within the intersection is equal to or greater than the input minimum excitation threshold, resulting in the selective activation of only those photosensitive elements that are present within the intersection and are of the targeted group.

In some examples, computing system 104 may use a set or series of radiation patterns that corresponds to a structure. For example, the radiation patterns of a series may correspond to cross sections of vasculature to be constructed in engineered tissue. Computing system 104 may retrieve a first radiation pattern of the series and system 100 may be used to build the corresponding cross section of the structure in a biological target (e.g., an engineered organ) through selective activation of photosensitive elements that are photo-adhesive, as described above. Computing system 104 may retrieve the second radiation pattern of the series and system 100 may be used to build the next corresponding cross section of the structure. This may be repeated until the structure or some portion thereof has been constructed. Alternatively, system 100 may be arranged as an assembly line with radiation sources 110/112 at multiple stations. Each station may emit beams according to a different radiation pattern of the series.

Engineered organs may be moved from station to station (e.g., on a conveyor), with each successive station being used to construct the next cross section of the structure. Alternatively, radiation patterns of a set may correspond to 3D parts of a structure, and each radiation pattern may be used to construct the structure over a series of steps. Again, this may be achieved using a single station or an assembly line arrangement.

Figure 2:
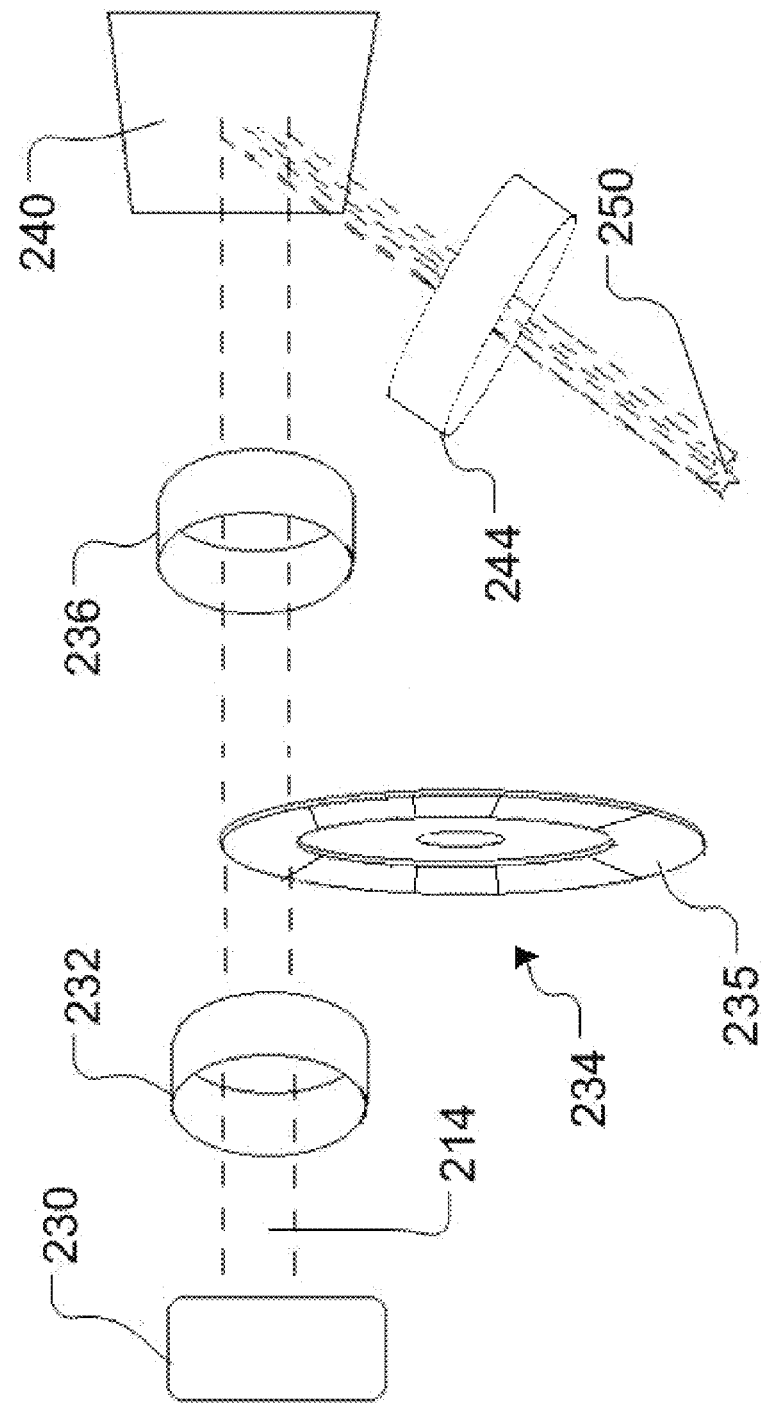
FIG. 2 illustrates a schematic diagram of shaped beam emission.

As discussed above, beams may be emitted or projected in various shapes to produce the desired beam intersection within the biological target. FIG. 2 illustrates a schematic diagram of an embodiment of shaped beam projection. A radiation source (e.g., radiation source 110/112) may include a radiation element 230, optical relay 232, color wheel 234 with filters 235, optical relay 236, reflector 240, and projection lens 244. Radiation source 230 may be a lamp or other source of EM radiation. Optical relays, color wheels, projection lenses, and similar devices are known in the art, and, thus, the detailed descriptions thereof are omitted for the simplicity of the description. Reflector 240 may include a reflective matrix, such as a micromirror array. For example, reflector 240 may be a digital micromirror device. The illustrated arrangement is merely one example, and other arrangements and combinations of components are also contemplated within the scope of this disclosure.

In operation, radiation element 230 may emit a beam 214 of EM radiation. Beam 214 may pass through optical relay 232, a filter 235 of color wheel 234, and optical relay 236 to reflector 240. Optical relays 232/236 may include one or more filters, such as a broad IR filter, a visible light filter, and/or a changeable filter. Reflector 240 may be controlled (e.g., by controller 108, as shown in FIG. 1) to selectively reflect one or more portions of beam 214 in a desired shape/radiation pattern 250 through projection lens 244. For example, shape/radiation pattern 250 may be formed by positioning the micromirrors of a digital micromirror device (i.e., reflector 240). The illustrated shape/radiation pattern (a star shape) is merely one example. Beams may be reflected in any shape/radiation pattern from one, two, or more locations and at varying angles to collectively produce an intersection with a desired 2D or 3D shape/radiation pattern within a target substrate. Color wheel 234 may include any number of filters 235, and each of the filters 235 may filter a different combination of wavelengths from beam 214. In one example, color wheel 234 may include three UV filters and three IR filters. In other examples, color wheel 234 may include any number and combination of UV filters, IR filters, and/or visible light filters. The IR and/or UV filters may be used alone or in various combinations to simultaneously activate different groups of photosensitive elements in one or more areas of the biological target.

Figure 3A:
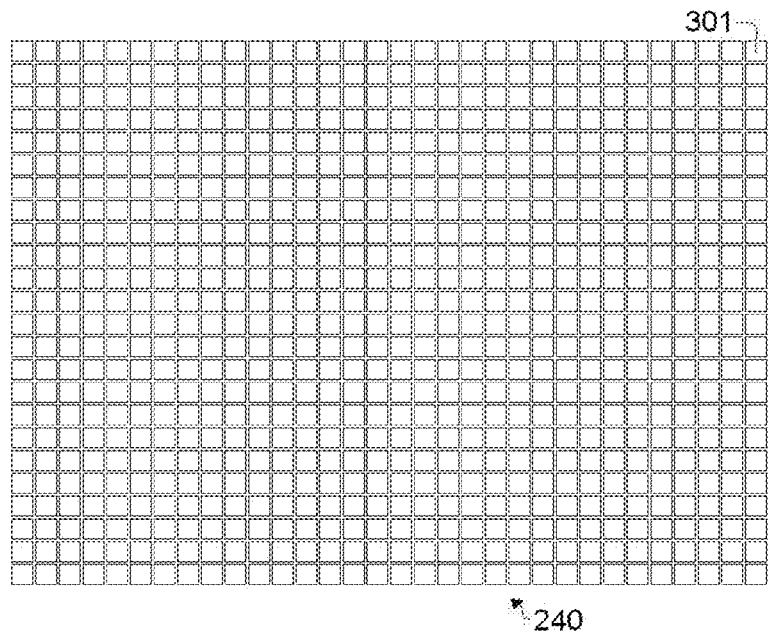
FIGS. 3a-3b illustrate schematic diagrams of the reflector of FIG. 2.
Figure 3B:
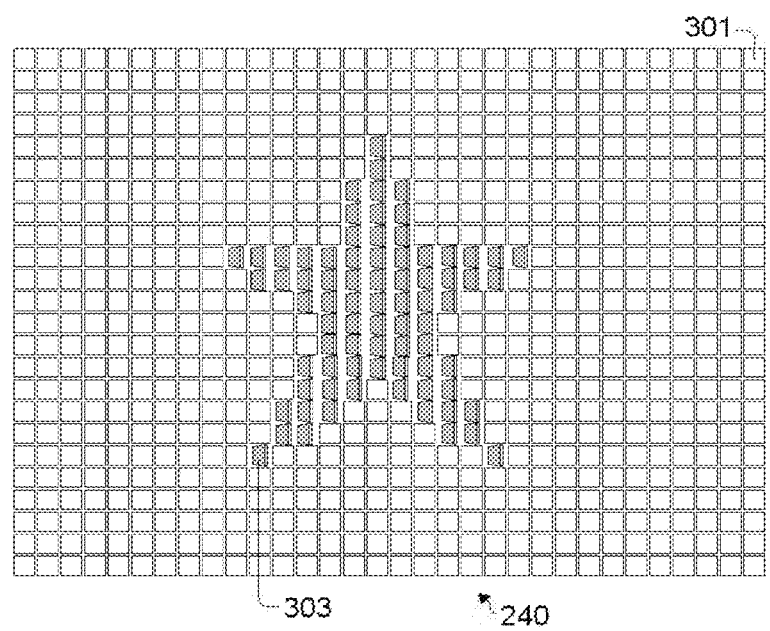

FIGS. 3a-3b illustrate schematic diagrams of the reflector of FIG. 2. Reflector 240 may include a plurality of reflective surfaces, such as micromirrors. The reflective surfaces may be individually switched between a first position (e.g., "off") and a second position (e.g., "on"). FIG. 3a shows all reflective surfaces in the first position (301). FIG. 3b shows some of the reflective surfaces switched to the second position (303) to reflect a beam of light in a desired shape. In the illustrated example, reflective surfaces in the second position (303) may reflect one or more beams of radiation (e.g., UV/IR) in the shape of a star. The number and arrangement of reflective surfaces may vary among examples. Reflector 240 may include a spatial light modulator (not shown), such as a micromirror array of a digital micromirror device. In other examples, reflector 240 may include one or more other spatial light modulators (not shown), such as a transmissive or reflective liquid crystal device (LCD).

Figure 4A:
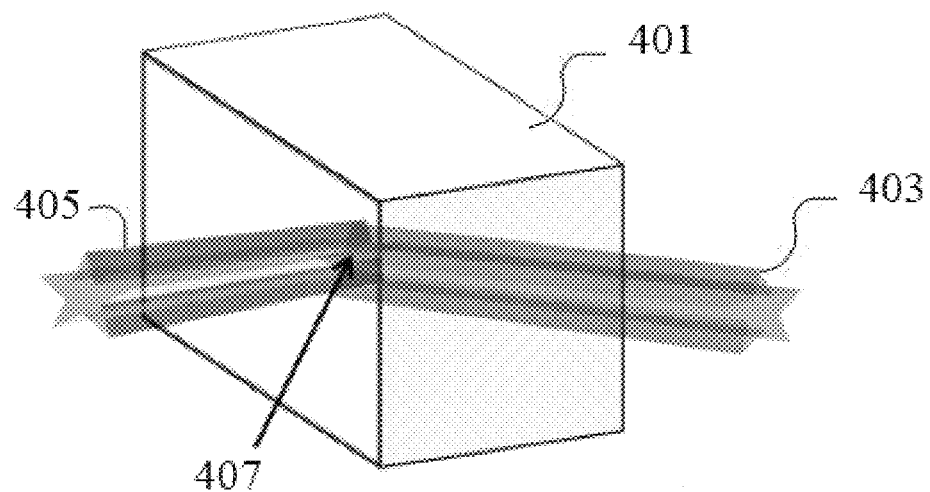
FIGS. 4a-4d illustrate beam intersections forming patterns within a target.
Figure 4B:
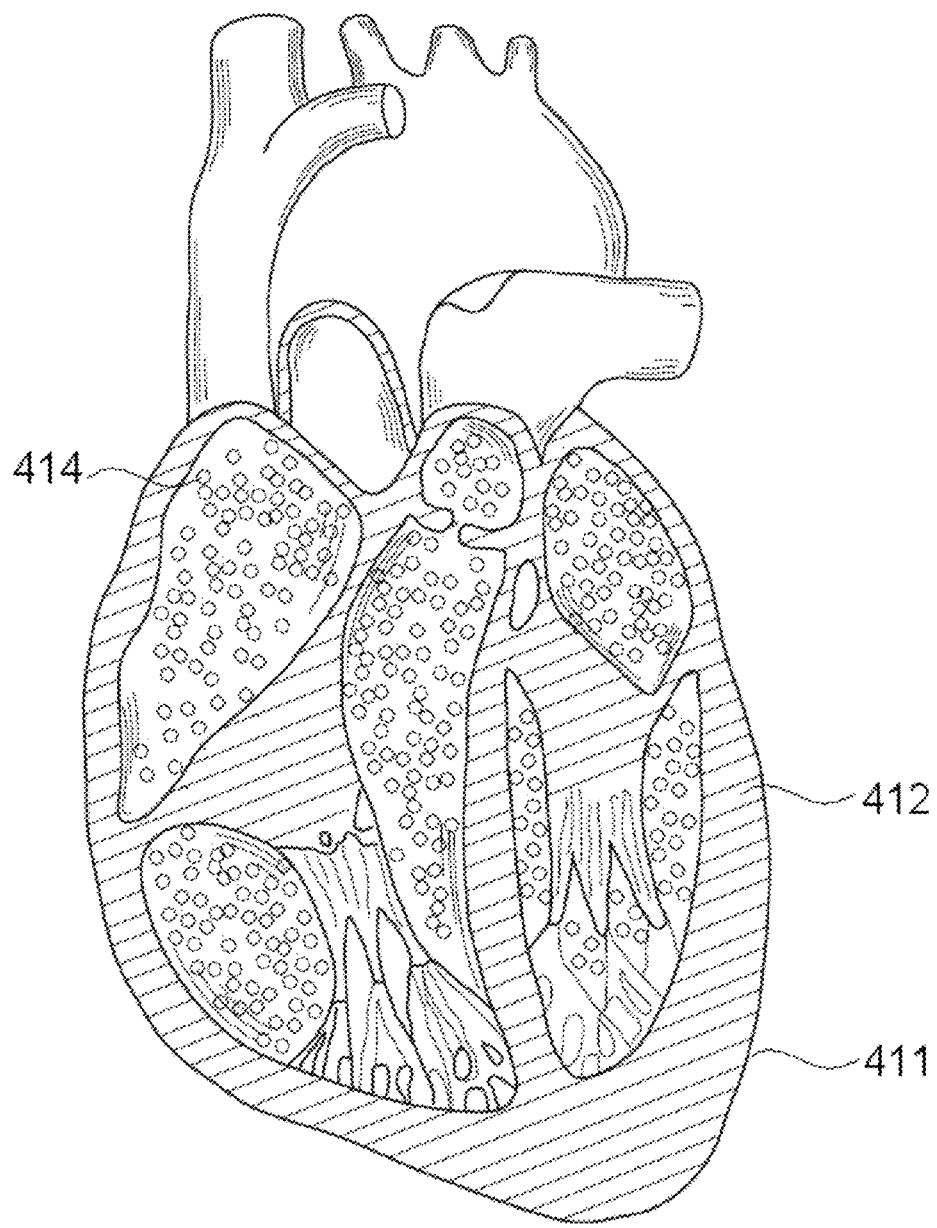
Figure 4C:
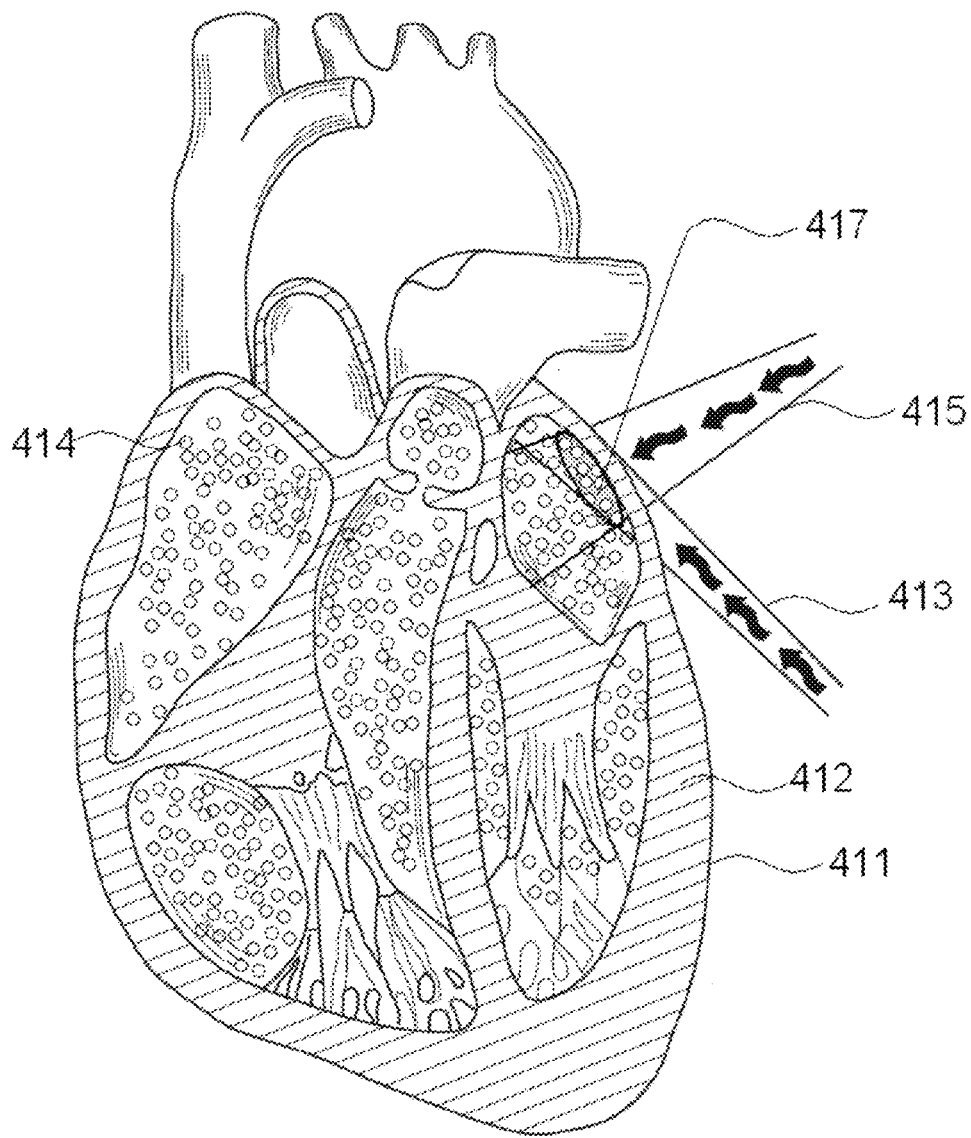

FIGS. 4a-4c illustrate examples of beam intersections forming radiation patterns within a target. As shown in FIG. 4a, one or more radiation sources, such as the radiation sources shown in FIG. 1, may emit first beam 403 and second beam 405 into biological target 401. First beam 403 and second beam 405 may intersect within the target, forming a 3D radiation pattern 407. Radiation may be emitted at any suitable wavelength, including but not limited to wavelengths within the ranges of 1 mm to 760 nm (infrared), 760 nm to 380 nm (visible), or 380 nm to 10 nm (ultraviolet).

First beam 403 may be emitted in any suitable shape to project a 2D radiation pattern on/in biological target 401 (e.g., a scaffold). Two, three, or more than three beams may be emitted to project a 3D radiation pattern into a 3D target such as an organ, a scaffold, and/or tissue. While biological target 401 is shown as a block of solid tissue, 3D radiation patterns may be projected within other types of targets. In one example, biological target 401 may be a scaffold constructed of connective tissue (e.g., collagen). The scaffold may be constructed de novo using known methods or by removing cells from a synthetic or donor organ as described above.

Figure 4D:
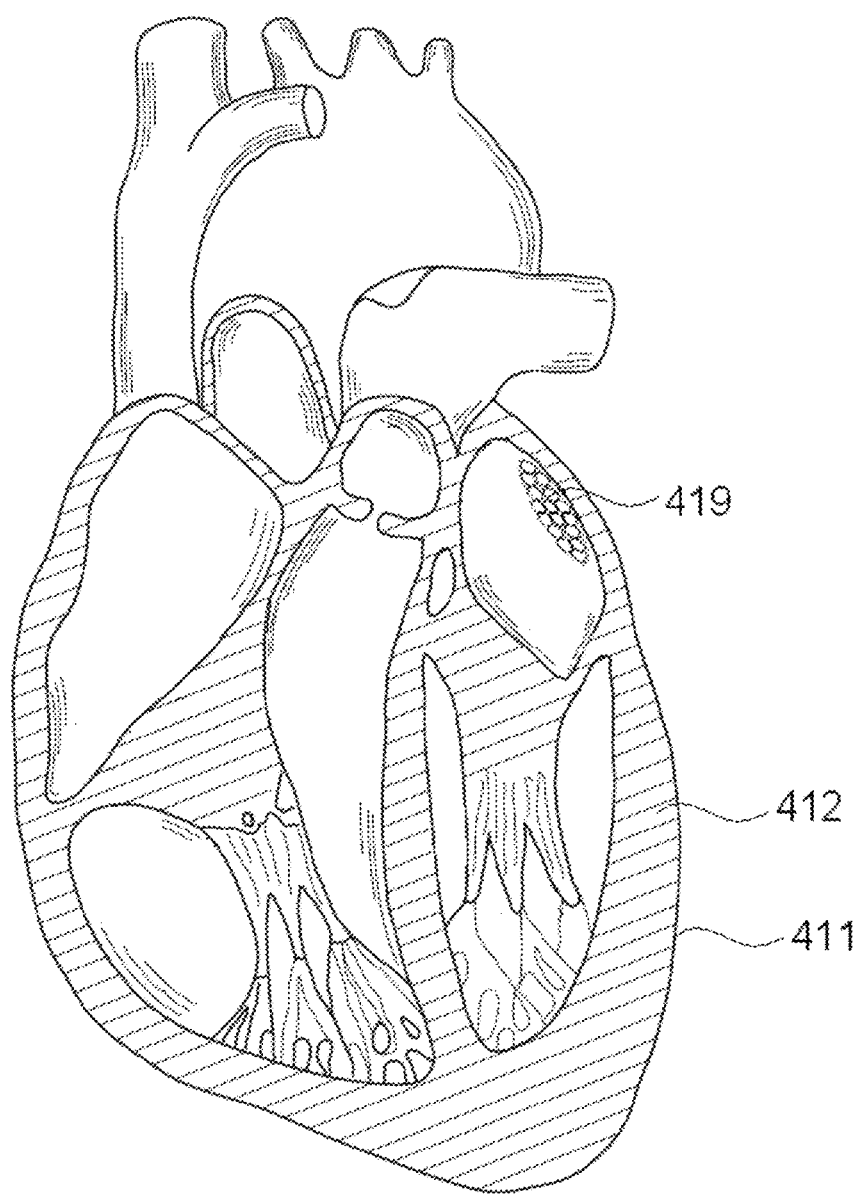

FIGS. 4b-4d show an example in which photosensitive elements are patterned within an organ scaffold. Scaffold 411 is prepared by removing cellular material from a donor organ (e.g., a heart) using a detergent solution as described above. The resulting scaffold 411 includes connective tissue 412, which remains substantially intact after removal of the cellular material. As shown in FIG. 4b, scaffold 411 is perfused with a solution containing photosensitive elements e.g. 414, which are photo-adhesive. Photosensitive elements 414 may include a biochemical factor coupled to a photo-adhesive molecule (e.g., an epidermal growth factor-azidobenzoic acid conjugate).

An image of the scaffold is provided to a radiation emission system (e.g., system 100), such as by scanning the scaffold or retrieving a pre-stored image from a memory or remote source. One or more areas of the image are selected manually or automatically. The selected areas are used by the radiation emission system to guide the emission of two or more beams of EM radiation into the scaffold along paths that intersect within a corresponding area of the target. Alternatively, a pre-stored image or radiation pattern is used by the radiation emission system to guide the emission of the beams. The wavelengths, directions, angles, shapes, intensities, and other characteristics of the beams are controlled and coordinated by the radiation emission system to reproduce the 2D or 3D radiation pattern within the scaffold.

FIG. 4c shows first radiation beam 413 and second radiation beam 415 intersecting within scaffold 411. In the illustrated example, the selected area of the target is a circular area on an interior surface of scaffold 411 (circled and shaded). The radiation dose received within the intersection meets or exceeds the minimum threshold dose required to activate photosensitive elements 414, causing adhesion of photosensitive elements 414 to scaffold 411 within intersection 417. As shown in FIG. 4d, the remaining non-adherent photosensitive elements 414 are then removed from scaffold 411 (e.g., by rinsing or flushing scaffold 411 with a liquid), leaving a desired biopattern 419. Examples of photosensitive elements and biopatterns are provided in FIGS. 5a-5e and in the accompanying description below.

Figure 5A:
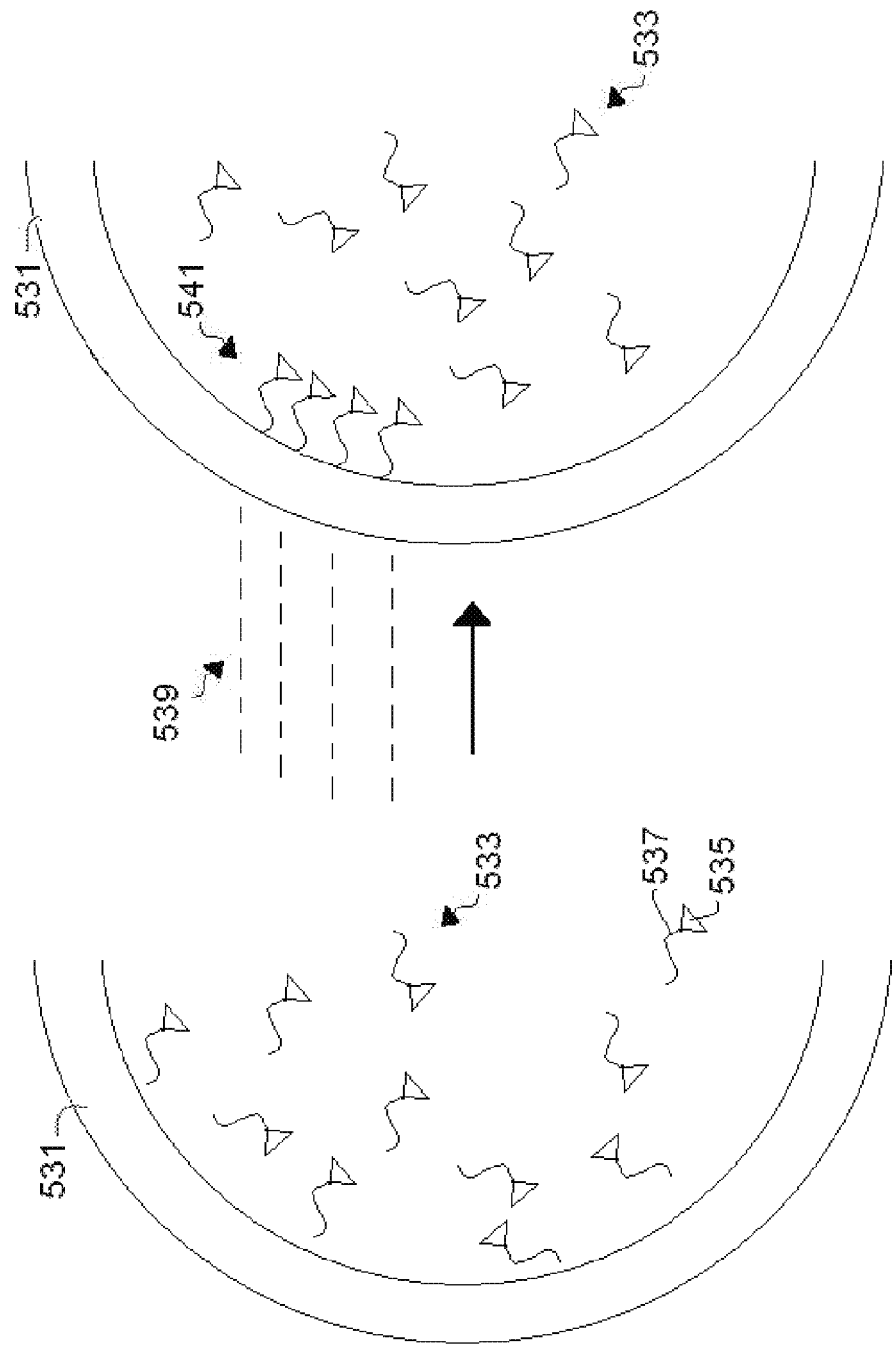

FIG. 5a shows photosensitive elements adhering to a scaffold 531. The illustrated photosensitive elements include a "patterning element" (e.g., a biochemical factor and/or a nanoparticle) that is coupled to a photo-adhesive molecule. In this example, each photosensitive element 533 includes patterning element 535 coupled to photo-adhesive molecule 537.

Photo-adhesive molecule 537 can include, but is not limited to, azidoaniline, polyoxyethylene, poly(acrylic acid), polystyrene, N-(4-azidobenzoyloxy)succinimide, 4-azidoaniline, a poly(anhydride-co-imide), a copolymer of N-vinyl pyrrolidone, poly(ethylene glycol) diacrylate, and/or another molecule that displays adhesive behavior in response to radiation exposure. Patterning element 535 can be coupled to photo-adhesive molecule 537 in any manner, including but not limited to a covalent bond, a linker molecule, etc. Poly (ethylene glycol) diacrylate is discussed in Nakayama and Matsuda, Photocurable surgical tissue adhesive glues composed of photoreactive gelatin and poly (ethylene glycol) diacrylate; Journal of Biomedical Materials, Vol. 48(4), pg. 511-521 (1999), incorporated by reference herein. Examples of photosensitive elements that are photo-adhesive are described in the following articles, which are incorporated by reference herein: Ito, "Tissue Engineering by Immobilized Growth Factors," *Mat. Sci. and Eng.* C6:267-274 (1998); Chen et al., "Photo-immobilization of Epidermal Growth Factor Enhances its Mitogenic Effect by Artificial Juxtacrine Signaling," *Biochimica et Biophysica Acta* 1358(2):200-208 (1997); Uhrich et al., "Synthesis and Characterization of Degradable Poly(anhydride-co-imides)" *Macromolecules* 28:2184-2193 (1995); and Park et al., (2000).

Patterning element 535 can be a biochemical factor including but not limited to a cytokine, chemokine, nucleic acid, enzyme, insulin, epidermal growth factor, nerve growth factor, heparin, etc., or a derivative of a biochemical factor. Examples of immobilized growth factors are described in Chen et al., (2000) and Ito, (1998).

Alternatively, patterning element 535 can be a nanoparticle. The activation wavelength of the nanoparticle may be different from the activation wavelength of photo-adhesive molecule 537. For example, patterning element 535 may be a hollow nanoparticle with an outer shell enclosing a biochemical factor or derivative thereof, a pharmaceutical compound/ drug, etc. The emission of EM radiation including the activation wavelength of photo-adhesive molecule 537 may be used to cause the adhesion of photosensitive element 533 to scaffold 531 without simultaneous activation of the nanoparticle. In another example, patterning element 535 is a nanoparticle with an outer shell, an internal core and one or more biochemical factors coupled to the exterior of the outer shell. The emission of EM radiation having the activation wavelength of photo-adhesive molecule 537, but not the activation wavelength of the nanoparticle, may be used to cause the adhesion of photosensitive element 533 to scaffold 531 without activating the nanoparticle. Activation of a hollow or solid nanoparticle may cause melting, degradation, and/or a conformational change of the nanoparticle, triggering the release of the enclosed and/or externally coupled biochemical factor. In some examples, activation of a photo-reactive nanoparticle may cause vibration and/or heating of the nanoparticle, triggering cell arrest/deletion.

Referring again to FIG. 5a, beams of EM radiation 539 with the activation wavelength of photo-adhesive molecules 537 (e.g., a wavelength in the UV, IR, NIR, or visible light range) may be emitted or projected into scaffold 531 as described above, causing photosensitive elements 533 within the intersection(s) of the beams to adhere to a surface of scaffold 531. Non-adherent photosensitive elements can be removed from scaffold 531 by any suitable method, such as by rinsing or dialysis, leaving adherent photosensitive elements 541. Scaffold 531 can be further rinsed with a second solution containing additional photosensitive elements that are photo-adhesive. The process may then be repeated with the same emitted radiation pattern or a new emitted radiation pattern, as shown in FIG. 5b.

Figure 5B:
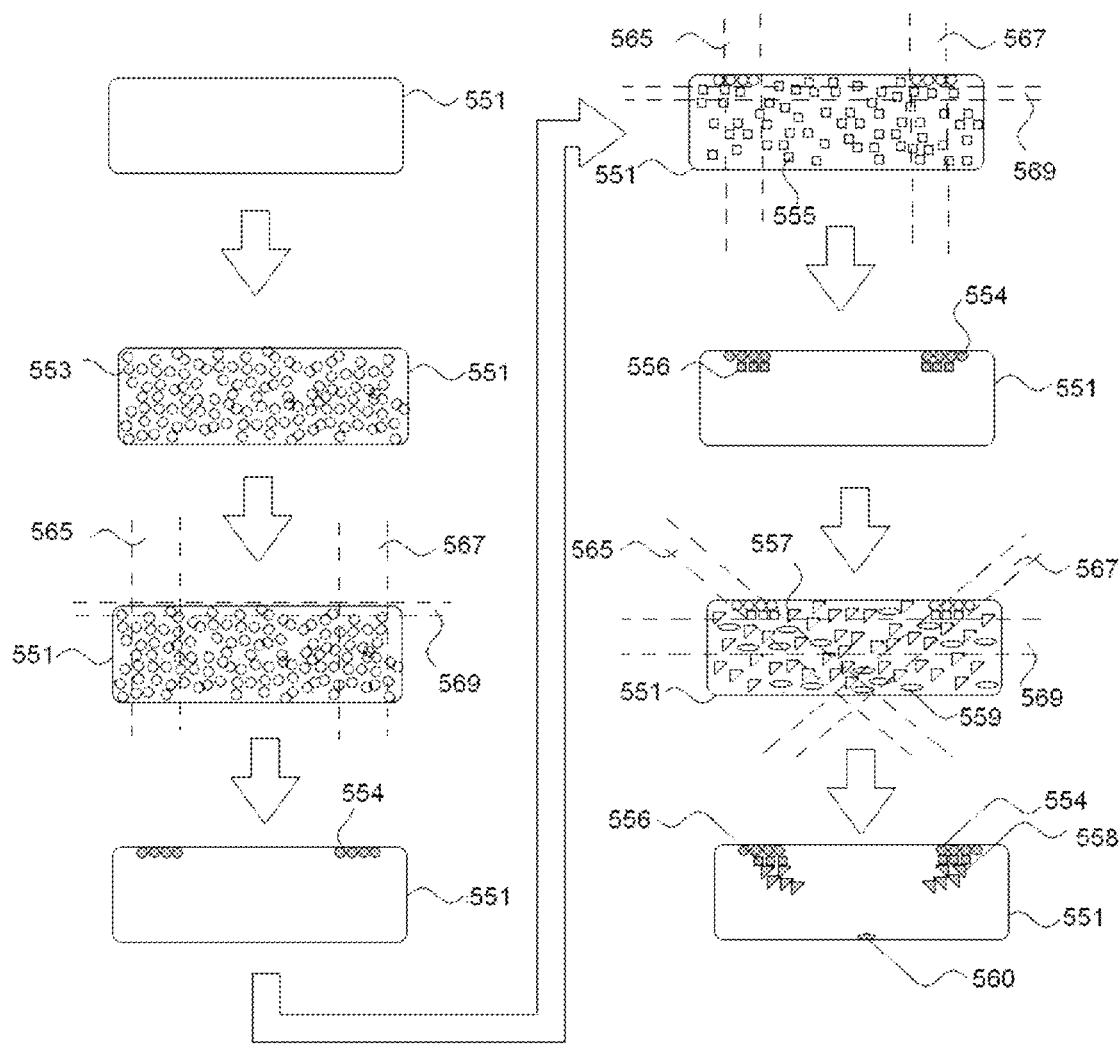

FIG. 5b is a schematic diagram illustrating the patterning of a 3D scaffold, shown in cross-section. The interior of scaffold 551 may be hollow, or the interior may be a matrix that is porous or permeable to photosensitive elements.

As illustrated, a first group of photosensitive elements 553 may be added to scaffold 551. First, second, and third radiation beams 565, 567, and 569 may be directed into scaffold 551 as described above, and may include radiation of the activation wavelength of photosensitive elements 553. In this example, the additive/combined energies of the first and third beams 567 and 569 may meet or exceed the minimum threshold dose required to activate photosensitive elements 553 within the intersection of those beams. Likewise, the additive/combined energies of the second and third beams 567 and 569 may meet or exceed the minimum threshold dose required to activate photosensitive elements 553 within the intersection of those beams. Activation of photosensitive elements 553 may cause them to adhere to scaffold 551 within the intersections. Non-adherent photosensitive elements 553 may be removed from scaffold 551, leaving first photosensitive element layer 554 in the areas of the beam intersections.

This process can be repeated with other photosensitive elements that are photo-adhesive, such as photosensitive elements 555. The positions, angles, wavelengths, and other characteristics of the emitted beams can be adjusted to reproduce a desired radiation pattern. For example, the radiation source may be a DMD with color wheel 234 as described above, and wavelength can be altered dynamically using a combination of different wavelength filters (e.g., filters 235). Angles may be determined and adjusted by a computing system and/or a controller (e.g., a DMD controller) based on the radiation pattern. In this example, the positions of beams 565, 567, and 569 are adjusted to create beam intersections adjacent to first photosensitive element layer 554. The non-adherent photosensitive elements 555 are then removed from scaffold 551, leaving a second photosensitive element layer 556 over first photosensitive element layer 554.

Two or more groups of photosensitive elements may be added to scaffold 551 concurrently. As shown, photosensitive elements 557 and 559 may be applied to scaffold 551 as a mixture. Photosensitive elements 557 may be responsive to a first activation wavelength while photosensitive elements 559 may be responsive to a second activation wavelength. The beams of radiation 565, 567, and 569 may be applied at different angles, wavelengths, etc. to build a 3D shape within scaffold 551. As an example, beams 565 and 567 may include both the first activation wavelength and the second activation wavelength, and beam 569 may include the first activation wavelength. Beams 565 and 567 may be adjusted to intersect with beam 569 in locations where adhesion of photosensitive elements 557 is desired. Beams 565 and 567 may also be adjusted to intersect with one another in another location where adhesion of photosensitive elements 559 is desired. The intensities and duration of emission of beams 565, 567 and 569 may be adjusted relative to one another such that photosensitive elements 557 that are in the path of only one of the beams receive less than the minimum threshold dose of radiation of the first activation wavelength, while photosensitive elements 557 in the intersection of beam 569 and either beam 565 or beam 567 are activated as a result of the combined energies of the beams. Likewise, each of beams 565 and 567 may carry insufficient energy of the second activation wavelength to activate photosensitive elements 559 that are in the path of only one of those beams, but in combination may deliver a sufficient radiation dose in the second activation wavelength to activate photosensitive elements 559 in the intersection of those beams. This may allow selective activation of different groups based on activation wavelength. For example, photosensitive elements 559 may be epidermal growth factor—azidobenzoic acid conjugates that adhere to the scaffold upon exposure to beams with wavelengths in the range of 380 nm to 10 nm (ultraviolet). Photosensitive elements 557 may be nanoparticles coupled to poly(anhydride-co-imides) that adhere to the scaffold upon exposure to beams with wavelengths in the range of 1 mm to 760 nm (infrared). Adjusting the beams 565, 567, and 569 to provide different wavelengths among intersections allows selective activation/adhesion of photosensitive elements 557 and 559.

Multiple photosensitive elements 554, 556, 558, and 560 that are photo-adhesive may be adhered in layers to construct complex 3D structures. The scaffold can be rinsed or immersed in a solution containing two or more types of photosensitive elements that are photo-adhesive (see e.g. FIG. 5b). Each type may be designed to adhere to the scaffold in response to a different wavelength and/or minimum threshold dose of radiation. Different areas may be selected within an image of the scaffold and used to guide emission of radiation patterns as described above. Thus, several areas of the scaffold can be patterned consecutively and/or concurrently with different photosensitive elements as desired. Various types of photo-adhesive photosensitive elements may be patterned within the scaffold to direct adhesion, differentiation, and/or other functions of cells subsequently added to the scaffold. For example, a biopattern may be created in a scaffold using photosensitive elements that include a nanoparticle, a cytokine enclosed by the nanoparticle, and a photo-adhesive molecule coupled to the nanoparticle. The photo-adhesive molecule may be activated with a first wavelength of light to adhere the photosensitive element to the scaffold. Cells may be added to the scaffold. As the cells grow and proliferate, the nanoparticle may be activated with a second wavelength of light to release the cytokine. The cytokine may trigger differentiation and/or metabolic changes in nearby cells.

In some examples, some or all of the photosensitive elements are (or include) nanoparticles. The nanoparticles may have various shapes and dimensions, each with a corresponding activation wavelength, to allow for differential activation of one or more groups of nanoparticles as desired. The photosensitive elements may also include photo-adhesive molecules (e.g., ortho-pyridyl-disulfide-n-hydroxysuccinimide polyethylene glycol polymer; see e.g. Loo et al., (2004)) coupled to nanoparticles and adhered to the scaffold using emitted EM radiation, as described above, prior to the addition of cells. As the cells form a tissue supported by the scaffold, the nanoparticles may be selectively activated using emitted EM radiation. Activation can cause localized heating, vibration, release of surface-bound biochemical factors, release of an enclosed biochemical factor (i.e., from a hollow nanoparticle), and/or induction of cell arrest/deletion in the targeted area. In some aspects, the activation of a nanoparticle may cause both the release of a biochemical factor and localized heating/vibration (see e.g., You (2010)).

Nanoparticles may lack a bound photo-adhesive molecule, and may instead be added to cells and/or a scaffold by another method such as by gas gun injection over a wide area. An apparatus and method for this technique is described in Groisman et al. U.S. Patent Application Pub. No. 2008/0206870, incorporated by reference herein. A radiation emission system (e.g., system 100) may then be used to direct a 3D radiation pattern into the target to activate the nanoparticles and cause heating, vibration, or a conformational change in the nanoparticles.

Nanoparticles may be surface-bound to a biological factor (e.g., a nucleic acid) that is released as a result of this activation. Alternatively, the nanoparticles may encapsulate a biochemical factor that is released by the conformational change (e.g., melting) of the nanoparticle. As still another alternative, the nanoparticles may lack an attached/encapsulated biochemical factor. These nanoparticles may be selectively activated to induce apoptosis of cells from within the cells through localized heating or vibration. Various combinations of nanoparticles and other photosensitive elements (e.g., photosensitive elements that are photo-adhesive) can be applied to the scaffold and differentially activated at desired times and locations to guide tissue development.

Figure 5C:
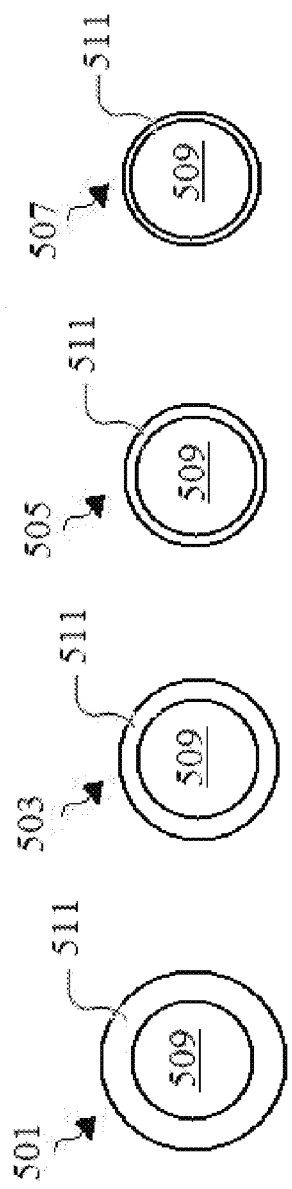
Figure 5D:
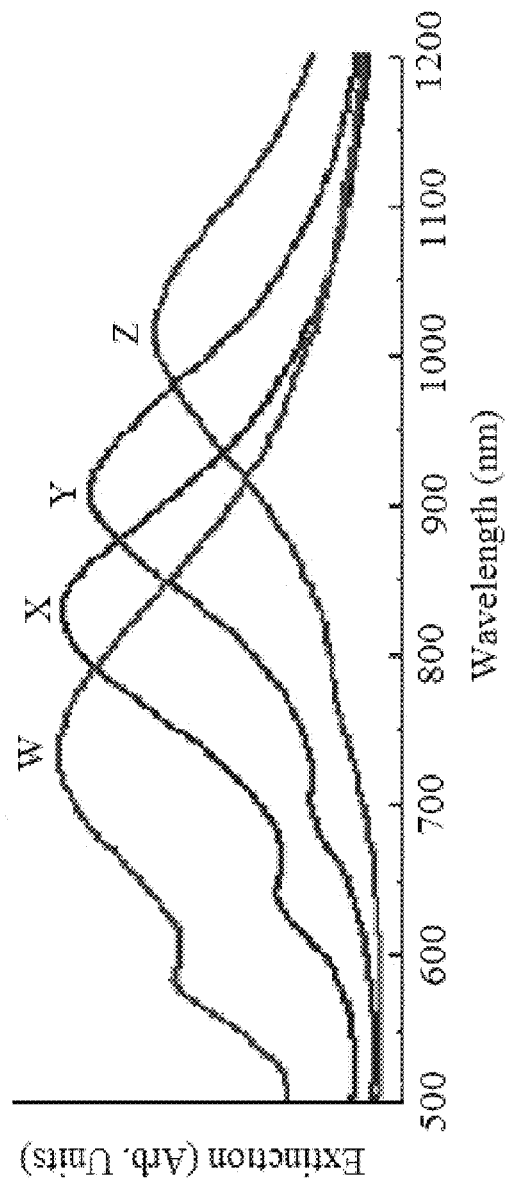

FIGS. 5c-5e illustrate various nanoparticle configurations. As shown in FIG. 5c, nanoparticles 501, 503, 505, and 507 can include a core 509 and an outer shell 511. Core 509 may include silica, iron oxide, gold, silver, carbon, calcium phosphate, iron oxide, magnetite, a polymer, and/or any other suitable material. The material for core 509 may be selected based on factors such as intended response to radiation (e.g., heating, vibration, rupture, etc.), biocompatibility, intended size/shape, and physical constraints. The diameter of core 509 may vary among examples, and may be within the range of 10-50 nm, 20-70 nm, 50-100 nm, or 100-250 nm. In some examples, core 509 may be absent. Nanoparticles lacking a core 509 may be hollow and may be designed to enclose a biochemical factor, as discussed above.

Outer shell 511 can include gold, silver, carbon, silica, calcium phosphate, iron oxide, magnetite, a polymer, or other biocompatible material, alone or in any combination. Outer shell 511 may have any thickness ranging from 1-120 nm, 5-50 nm, or 20-100 nm. Materials may be selected for construction of nanoparticles based on the desired activation behavior. For example, nanoparticles designed to release surface-bound biochemical factors in response to activation with radiation may be constructed with an outer shell of gold and a silica core, while nanoparticles designed to release an enclosed biochemical factor in response to a radiation dose may have an outer shell of gold without an inner core. Nanoparticles may be provided in various sizes and shapes, as described for example in Loo (2004) and Chen (2006).

The outer dimensions of nanoparticles may be sized/shaped to maximize nanoparticle uptake in a biological target. Nanoparticles may be provided in a particular size and shape for maximum uptake in a particular organ within a human body (e.g., the bladder, the liver, etc.), as described for example by De Jong et al., "Particle Size-dependent Organ Distribution of Gold Nanoparticles after Intravenous Administration," *Biomaterials* 29:1912-1919 (2008), incorporated by reference herein. Other nanoparticles may be rod-shaped and may exhibit a conformational change, such as a change to a spherical shape, upon activation. The conformational change may cause the release of a surface-bound molecule such as a nucleic acid.

The dimensions of outer shell 511 and/or core 509 may also be varied in order to influence the wavelength absorption among nanoparticle varieties. In the example illustrated by FIG. 5c, nanoparticles 501, 503, 505, and 507 include core 509 with a diameter of approximately 60 nanometers (60 nm). Outer shell 511 may be approximately 20 nm thick in nanoparticle 501, approximately 10 nm thick in nanoparticle 503, approximately 7 nm thick in nanoparticle 505, and approximately 5 nm thick in nanoparticle 507. The variations in outer shell thickness may cause each of nanoparticles 501, 503, 505, and 507 to be activated by different wavelengths, as shown in FIGS. 5*c-d*.

FIG. 5*d* illustrates the absorption spectra of the nanoparticles of FIG. 5*b*, with each peak (W, X, Y, Z) indicating the activation wavelength of the corresponding nanoparticle (501, 503, 505, and 507, respectively). Two or more nanoparticle varieties may thus have a different outer shell thickness, allowing each variety to be differentially triggered by the application of the corresponding activation wavelength. As described above, the nanoparticles can also be differentially triggered by location using radiation patterns intersecting at the desired location(s) and in the desired shape within the target. In one example, at least a first, a second, a third, and a fourth variety of nanoparticles may be provided.

Referring now to FIG. 5*e*, nanoparticles may be provided in one or more shapes. The nanoparticle shapes illustrated are provided merely as examples, and are not intended to be limiting. In one example, a nanoparticle may have two ends connected by a tapered or narrow center (e.g., nanoparticle 513). Another example is a rod shape (e.g., nanoparticle 515). Still another example is a hollow spherical shell (e.g. nanoparticle 517). A nanoparticle may also have two ends and a wider center, such as nanoparticle 519.

A hollow nanoparticle, such as nanoparticle 517, may enclose one or more molecules 521. Molecules 521 may be non-bondable materials that are encapsulated by the hollow nanoparticle during fabrication of the nanoparticle. They may be released by the nanoparticle in response to exposure of the nanoparticle to the activation wavelength. The release may occur through physical rupture, melting, degradation over time, enhanced degradation in response to EM radiation of an activation wavelength, or other alteration of the hollow nanoparticle. In some examples, molecules 521 can include one or more biochemical factors such as, but not limited to, a nucleic acid, a protein, a lipid, a carbohydrate, an enzyme, a growth factor, a cytokine, and/or other molecule.

Some nanoparticles may be coupled to a molecule 525, such as a growth factor, either directly or via a coupling factor 523. For example, DNA can be bound to a gold surface of a nanoparticle directly through thiol end groups. The nanoparticle may then be incorporated by a cell. When EM radiation is applied to the cell at the activation wavelength of the nanoparticle, the bound DNA may be released within the cell for incorporation into the cellular DNA and/or expression of an encoded product. In another example, a protein may be attached to an oligonucleotide anchored to the nanoparticle surface (adhesively or through thiol groups). In still another example, an intracellular localization sequence/motif may be coupled to the nanoparticle surface and may cause the nanoparticle to be directed to one or more locations or organelles within the cell (e.g., the nucleus, mitochondria, etc.).

Nanoparticles may be incorporated into a scaffold and/or into cells by any known method. For example, nanoparticles may be incorporated into a scaffold by washing/incubating the scaffold in a liquid or semi-liquid medium containing the nanoparticles. In another example, nanoparticles may be incorporated into a scaffold or into cells by gas gun injection over a relatively wide area. In still other examples, nanoparticles in a solution may be provided to cells and the cells may be incubated and/or electroporated to induce uptake of the nanoparticles. Alternatively, a viral vector may be used to deliver the nanoparticles to cells, before or after addition of the cells to the scaffold. A viral vector or a molecule adhered to the surface of the nanoparticles may be used to target delivery of the nanoparticles to specific cells within a tissue, organ, or other biological target.

Nanoparticles may be introduced into a tissue, an organ, and/or other biological target without prior incorporation into a cell. The nanoparticles may be introduced by gas gun injection, viral vector, electroporation, passive uptake, endocytosis, phagocytosis, or any other known method. EM radiation may then be applied to a desired location within the tissue, organ, and/or other biological target according to a radiation pattern, as described above, to selectively release a coupled/encapsulated molecule (e.g. a growth factor, nucleic acid, enzyme, etc.). The wavelength may be adjusted over the desired area to selectively activate one nanoparticle variety without activation of nanoparticle varieties responsive to different activation wavelengths.

In some examples, the radiation/beams may be applied in short pulses to prevent overheating of the nanoparticles and to prevent cell damage in non-targeted areas of tissue. The radiation/beams may be applied for a longer duration for some purposes, such as for selective deletion of cells by heating of nanoparticles within the cells or adhered to a scaffold. In one example, the duration may be increased to cause degradation of hollow nanoparticles and release of a biochemical factor enclosed therein. In another example, the duration may be decreased to cause a conformational change of a nanoparticle resulting in the release of a nucleic acid coupled to the surface of the nanoparticle.

In still another example, hollow nanoparticles with one or more enclosed biochemical factors and externally coupled targeting factors (e.g., antibodies) may be introduced into a scaffold/tissue. Once the nanoparticles have reached their intended target, EM radiation of the activation wavelength may be applied to the target to cause melting or degradation of the nanoparticle and release of the enclosed biochemical factor(s). Alternatively, EM radiation may be applied at a dose that exceeds a minimum threshold level for removal of the targeting factor from the exterior surface of the nanoparticle, but does not exceed a minimum threshold level for release of the enclosed biochemical factor(s). The nanoparticles may then be allowed to degrade without additional radiation, releasing the enclosed biochemical factors over an extended period, or may be activated with a higher dose of EM radiation as desired.

Some nanoparticles may be left in the tissue over extended periods of time. Other nanoparticles may be activated to release coupled growth factors once tissue development has progressed sufficiently that it will not be adversely affected by the release of the growth factors. Activation of nanoparticles to release growth factors during later stages of tissue development may be done in order to prevent uncontrolled release at a later time (e.g., when the tissue has been placed into a living body).

Figure 6A:
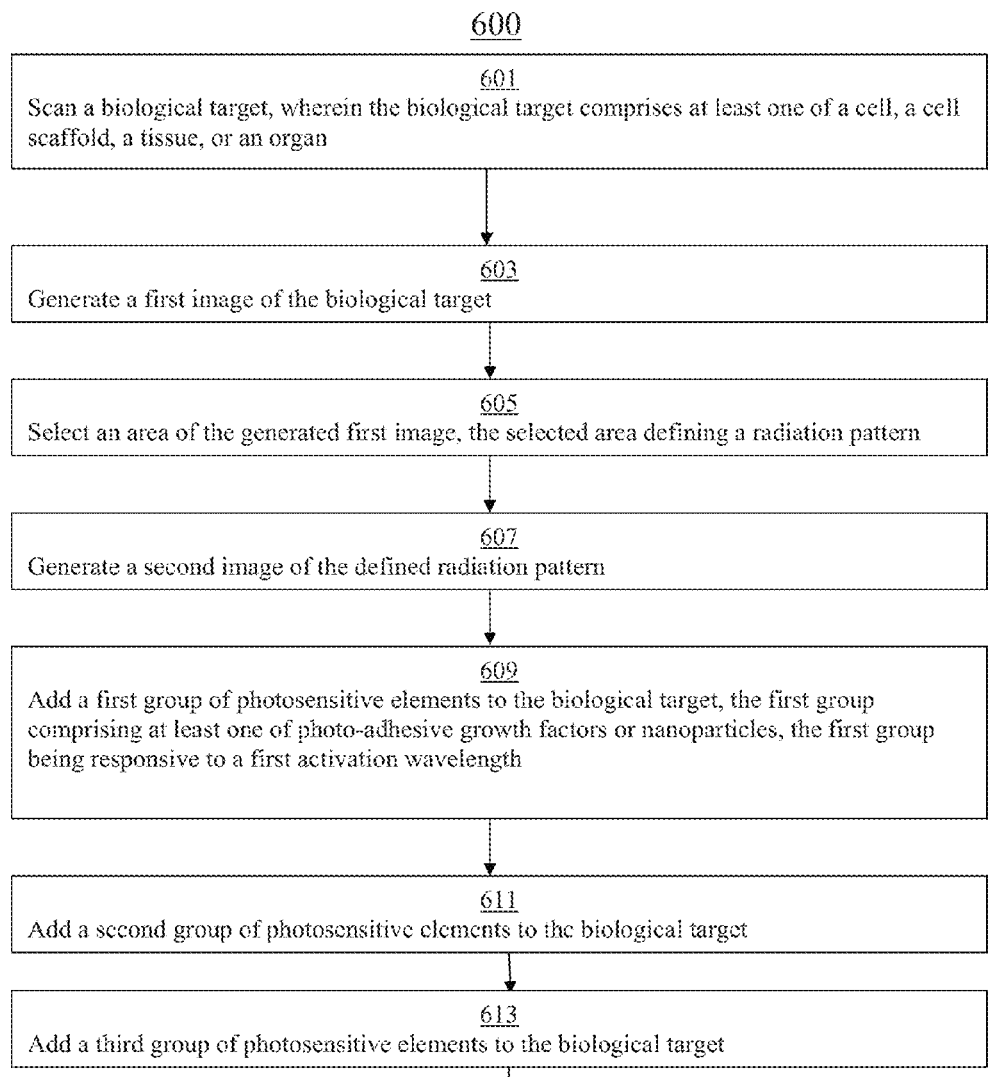
FIG. 6 illustrates a flow chart of a method for selective 3D biopatterning.
Figure 6B:
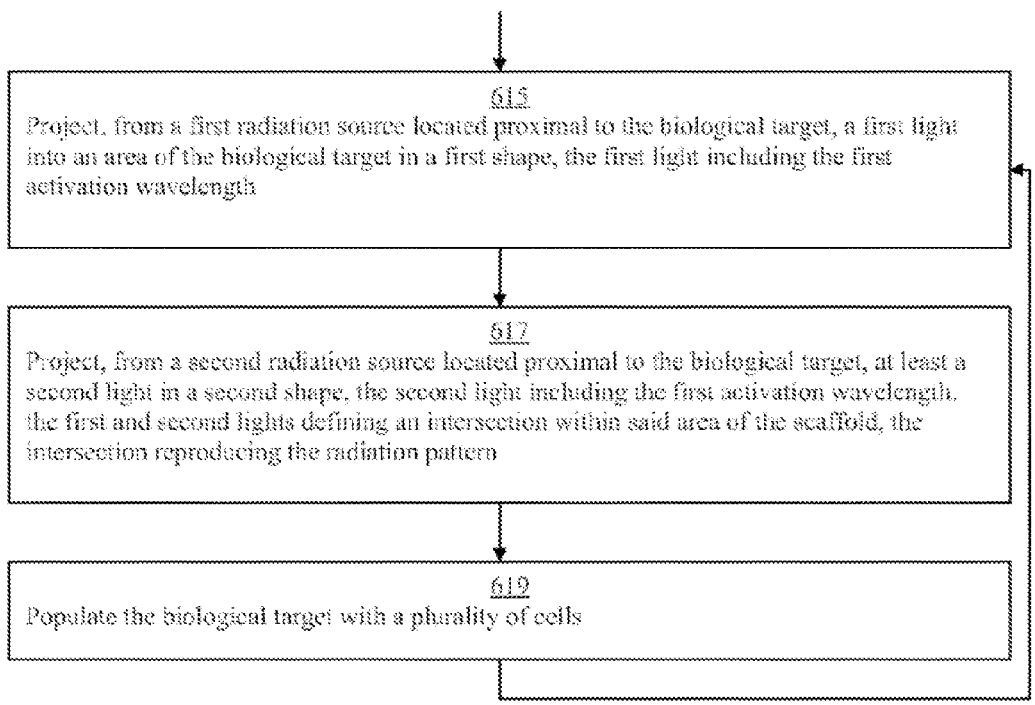

FIG. 6 illustrates a flow chart of an embodiment of a method for selective 3D biopatterning. It will also be appreciated that in some examples various blocks may be repeated, eliminated, divided into additional blocks, reordered, and/or combined with other blocks. For example, method 600 may be used for selective 3D biopatterning of growth factors on a scaffold without block 619. One or more blocks of the method may then be repeated to direct tissue development using that scaffold and added cells as starting materials. Thus, in this example, the "photosensitive elements" may be photo-adhesive growth factors in one block, and the blocks may be repeated with nanoparticles as the "photosensitive elements." Method 600 may begin at block 601.

At block 601, a biological target may be scanned. The biological target may include at least one of a scaffold, a tissue, an organ, or a body. The biological target may be scanned or imaged by any imaging device (e.g., imager 102 shown in FIG. 1) known in the art, such as a CT scanner, MRI scanner, X-ray device, etc.

At block 603, a first image of the biological target may be generated. Some examples may lack a block 601 and/or block 603. For example, an image of a biological target may be provided separately (e.g. an image from a previous scan or provided images of the biological target) and method 600 may begin at block 605. The first image can be a 3D image. Alternatively, the first image may include one or more 2D images, which may be combined or processed (e.g., by a computing system using a 3D modeling/reconstruction algorithm) to form the first 3D image.

Optionally, at block 605, an area of the generated first image may be selected in any suitable manner, as discussed above with reference to FIG. 1. The selected area may define a radiation pattern. In some examples a computing device (e.g., computing system 104 shown in FIG. 1) may select the area automatically. In other examples, a user may select the area using an input device of a display and/or computing device. The selected area can be a 3D area of the first image, and the radiation pattern can be a 3D pattern. Alternatively, a radiation pattern may be pre-stored or retrieved for use without blocks 601, 603, and/or 605.

Optionally, at block 607, a second image may be generated of the defined radiation pattern. The second image can be a 3D image. In some examples, the second image may include one or more 2D images that can be combined to form a 3D image. Any or all of blocks 601-607 may be performed automatically by a system such as system 100 (see e.g. FIG. 1 and accompanying description above). In those examples, method 600 may begin at block 609. In some examples, any or all of blocks 601-607 may be omitted and a pre-stored radiation pattern or image may be used instead. In such examples, method 600 may begin at block 609.

At block 609, a first group of photosensitive elements may be added to the biological target. The first group may include photo-adhesive components and/or nanoparticles. The first group may be responsive to a first activation wavelength. In some examples, the first group may also have a first minimum threshold dose for activation of the photosensitive elements. At least some of the photosensitive elements of the first group may be coupled to one or more growth factors. These photosensitive elements may be configured to release the growth factors in response to exposure to EM radiation of the first activation wavelength. Further, at least some of the photosensitive elements of the first group may be selectively targeted to a specific cell type (e.g. by surface-bound antibodies, etc.). In one example, the photosensitive elements in block 609 may be photo-adhesive biochemical factors (e.g., photo-adhesive growth factors) and the biological target may be a scaffold.

Addition of the photosensitive elements can occur in any suitable manner. For example, where the biological target is a cell or tissue, addition may occur by electroporation, active uptake, gas gun injection, viral vector, and/or other methods previously described or known in the art.

Optionally, at block 611, a second group of photosensitive elements may be added to the biological target. The second group of photosensitive elements may include photo-adhesive components and/or nanoparticles. The second group may be responsive to a second activation wavelength. In some examples, the second activation wavelength may be greater than the first activation wavelength, allowing differential activation within the same tissue location. The first and second groups of photosensitive elements may be selectively activated to form a 3D structure (e.g., sequential layers of photosensitive elements that are photo-adhesive). In some examples, block 611 may be omitted.

Optionally, at block 613, a third group of photosensitive elements may be added to the biological target. The third group may include photo-adhesive components and/or nanoparticles, and may be responsive to a third activation wavelength. As described above, one or more blocks of method 600 may be repeated to layer groups of photosensitive elements within structures within a de-celled organ or constructed scaffold. Groups of photosensitive elements may be responsive to different activation wavelengths and/or may have different minimum thresholds for activation, allowing the selective activation of individual groups. In some examples, block 611 may be omitted.

Blocks 609, 611 and/or 613 may occur sequentially or concurrently and in any order. In one example, two or more groups may be added to the scaffold concurrently in the same solution, and each group may have a different activation wavelength. The groups may then be differentially activated or adhered to the scaffold by applying EM radiation of each of the activation wavelengths in accordance with the radiation pattern. For example, adhesion of different groups of photosensitive elements may be desired within different intersections of the same radiation pattern. The wavelengths of the beams may be adjusted relative to one another in to deliver the first activation wavelength within the first intersection and to deliver the second activation wavelength within the second intersection (see e.g. FIG. 5*b*). Alternatively, each group may be added separately, with the method proceeding to block 615/617 after each addition, to adhere each group to the scaffold separately from other groups (see e.g. FIG. 5*b*). The wavelengths of the beams may be adjusted to deliver two or more activation wavelength(s) within each intersection.

In some embodiments, a scaffold may be provided with various photosensitive elements within, but not adhered to, the scaffold. For example, a scaffold may be provided in a solution containing photosensitive elements. In other embodiments, a scaffold, tissue, organ, or other biological target may be provided with various photosensitive elements already adhered or otherwise positioned on or within the biological target. In these examples, the method 600 may begin at block 615.

At block 615, emit, from a first radiation source located proximal to the biological target, a first beam of light may be emitted into an area of the biological target in a first shape and at a first wavelength. The first radiation source may be located proximal to the biological target. In some examples, the first shape may be based at least partially on the second image, and the area of the biological target may correspond to the selected area of the first image. In other examples, the first shape may be based instead on a pre-stored, retrieved, or received radiation pattern or image. As shown in FIGS. 1, 2, and 3, the first beam may be projected into the biological target without the use of a pattern mask. Where a 2D area is desired, the contours of the selected area (or radiation pattern) may be reproduced on or in the target by the first beam. Alternatively, where a second beam is used, the first shape may complement the shape of the second beam in order to reproduce the contours of the selected area and/or the radiation pattern. The first beam may have one or more wavelengths, including the first activation wavelength. The first beam may deliver sufficient energy of the first activation wavelength to exceed a minimum threshold dose of the first group of photosensitive elements. Alternatively, the first beam may provide insufficient energy of the first wavelength to activate the photosensitive elements of the first group, and the combined energies of the first beam and the second beam (which also includes the first wavelength) may activate the photosensitive elements in the beam intersection.

Emitting the EM radiation may include pulsing the first beam. For example, the EM radiation may be emitted by a DMD, which inherently pulses and changes the "brightness" of an image. This effectively changes the pulse frequency and emitted/projected radiation pattern. In another example, the EM radiation may be emitted by a LCD or DMD projector that is provided (e.g., by a computing system) with a moving graphic to project, causing rapid shape change. In still another example, for very high speed pulses, the radiation source may be a laser, diode, or flashlamp that is pulsed in order to limit heating and prevent tissue damage. In other examples, EM radiation (e.g., visible or non-visible light) may be emitted into the target according to a pre-stored, received, or retrieved radiation pattern without pulsing the first beam.

At block 617, at least a second beam of light may be emitted in a second shape at a second activation wavelength. The first and second beams may define an intersection within the area of the scaffold, and the intersection may reproduce the selected area and/or radiation pattern. The second beam of light may be emitted from a second radiation source located proximal to the biological target. Alternatively, the second beam of light may be emitted by the first radiation source.

In block 619, one, two or more than two radiation sources and/or projectors can be used to emit any number of beams to reproduce a desired 3D radiation pattern within a volume of a biological target (e.g., within solid tissue, within an organ, within a scaffold, etc.). This may allow selective mapping of one or more of the groups of photosensitive elements within the scaffold to direct tissue development. The first and second beams may include the activation wavelength(s) of the photosensitive elements to be activated. In some examples, the first and second beams may collectively carry sufficient EM radiation of the activation wavelengths to exceed the minimum threshold dose of the targeted photosensitive elements within the intersection of the beams. Emitting the second beam may further include pulsing the second beam. For example, where the biological target is a tissue, any or all of the beams may be delivered in short pulses to minimize radiation damage to non-targeted areas of the tissue.

Any or all of the beams may also be repositioned between pulses to repeatedly deliver the intended radiation dose while varying the portions of surrounding non-target tissue exposed to the beams. This may include reconfiguring the shapes, wavelengths, angles, and other characteristics of the beams relative to one another and to the biological target with each repositioning of the beams. This may be done, for example, based on a continuous input of image data from an imager. The image data may be used by a computing system and/or controller to track the motion of a moving biological target (e.g., a beating heart) and dynamically reconfigure the beams and/or beam intersections accordingly. This could be done in order to pattern a beating heart or to selectively activate photosensitive elements in an area of a beating heart.

In some embodiments, the method may return to block 609 after block 615/617 and blocks 609, 611, 613, and/or 615/617 may be repeated. For example, the photosensitive elements may be nanoparticles targeted to a portion of the biological target by surface antibodies or nanoparticle size. In blocks 615/617, the nanoparticles may be activated to cause arrest/deletion of nearby cells within that portion of the biological target. Any or all of blocks 609-617 may be repeated with additional nanoparticles to cause arrest/deletion of additional cells within the targeted area. In other examples, any or all of blocks 609-617 may be repeated one or more times before proceeding to block 619. This may be done to produce layers of photosensitive elements, to pattern additional photosensitive elements within the scaffold, and/or to create 3D structures within the scaffold using photosensitive elements.

At block 619, the biological target may be populated with a plurality of cells. The plurality of cells may include a single cell type. Alternatively, the plurality of cells may include two or more cell types. For example, at least one of the cell types may be a differentiated cell type. Alternatively, at least some of the plurality of cells may be stem cells. As used herein, a "stem cell" can be any totipotent, pluripotent, or multipotent cell, and a "differentiated cell" can be any cell that is partially or terminally differentiated.

At least some of the cells of the plurality may include nanoparticles and/or nanoparticles coupled to a growth factor. In one example, terminally differentiated cells may be added to a scaffold that has been patterned with photosensitive elements that include a photo-adhesive component coupled to one or more growth factors. The mapping function provided by the patterned scaffold may direct the terminally differentiated cells to adhere and proliferate in the correct locations of the scaffold, reducing or eliminating the need for stem cells. In this example, a patient's own terminally differentiated cells may be used to populate the scaffold to form a tissue (e.g. a replacement heart, kidney, skin, eye, bone, or other tissue or organ).

In some examples, blocks 615 and/or 617 may be repeated after block 619 to activate photosensitive elements after addition of cells to the scaffold. Cells that proliferate excessively or in an undesired location can be selectively deleted by activating nanoparticles positioned within the cells and/or on or within the scaffold. Nanoparticles may also be selectively activated to guide differentiation of the cells, such as by triggering release of biochemical factors from the nanoparticles. In one example, photosensitive factors may be selectively adhered to a scaffold in a biopattern, and cells may then be added to the scaffold and allowed to proliferate to form a tissue. Cells in selected areas of the tissue may then be deleted by activating nanoparticles within the selected areas, or growth factors may be released within areas of the tissue by activating nanoparticles within those areas.

Photosensitive elements may also be added to the cells after addition of the cells to the scaffold. For example, hollow nanoparticles enclosing nucleic acids in a cavity surrounded by an outer shell may be added to cells by gas gun injection after the cells are added to the scaffold. The cells may proliferate to form a tissue. Nanoparticles within an area of the tissue may be selectively activated with EM radiation at a later time, triggering release of the nucleic acids within those cells.

FIG. 7 is a block diagram illustrating an example computing system configured as in FIG. 1. In a very basic configuration 701, computing system 700 typically includes one or more processors 710 and system memory 720. A memory bus 730 may be used for communicating between processor 710 and system memory 720.

Depending on the desired configuration, processor 710 may be of any type including but not limited to a microprocessor (µP), a microcontroller (µC), a digital signal processor (DSP), or any combination thereof. Processor 710 may include one more levels of caching, such as a level one cache 711 and a level two cache 712, a processor core 713, and registers 714. An example processor core 713 may include an arithmetic logic unit (ALU), a floating point unit (FPU), a digital signal processing core (DSP Core), or any combination thereof. An example memory controller 715 may also be used with the processor 710, or in some implementations memory controller 715 may be an internal part of processor 710.

Depending on the desired configuration, system memory 720 may be of any type including but not limited to volatile memory (such as RAM), non-volatile memory (such as ROM, flash memory, etc.) or any combination thereof. System memory 720 may include an operating system 721, one or more applications 722, and program data 724. Application 722 may include programming instructions providing logic to implement the above described biopatterning. The programming instructions may provide, for example, logic to select and/or facilitate selection of a 2D or 3D area within a displayed image of a biological target. Program Data 724 may include radiation wavelengths, pulse durations, and other related values.

Computing system 700 may have additional features or functionality, and additional interfaces to facilitate communications between basic configuration 701 and any required devices and interfaces. For example, a bus/interface controller 740 may be used to facilitate communications between basic configuration 701 and one or more data storage devices 750 via a storage interface bus 741. Data storage devices 750 may be removable storage devices 751, non-removable storage devices 752, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and non-volatile, removable and non-removable media implemented in any method or technology for storage of information, such as computer readable instructions, data structures, program modules, or other data.

System memory 720, removable storage 751 and non-removable storage 752 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing system 700. Any such computer storage media may be part of device 700.

Computing system 700 may also include an interface bus 742 for facilitating communication from various interface devices (e.g., output interfaces, peripheral interfaces, and communication interfaces) to basic configuration 701 via bus/interface controller 740. Example output devices 760 include a graphics processing unit 761 and an audio processing unit 762, which may be configured to communicate to various external devices such as a display (e.g., a 3D display) or speakers via one or more A/V ports 763. Example peripheral interfaces 770 include a serial interface controller 771 or a parallel interface controller 772, which may be configured to communicate with external devices such as input devices (e.g., keyboard, mouse, pen, voice input device, touch input device, etc.) or other peripheral devices (e.g., a scanner/imager, a controller, a radiation projector, etc.) via one or more I/O ports 773. An example communication device 780 includes a network controller 781, which may be arranged to facilitate communications with one or more other computing devices 790 over a network communication link via one or more communication ports 782.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing system 700 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing system 700 may also be implemented as a personal computer including both laptop computer and non-laptop computer configurations.

The herein described subject matter sometimes illustrates different components or elements contained within, coupled to, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or Figures, should be understood to contemplate the possibilities of including one of the terms, either of the terms, or both terms. For example, the phrase "A or B" will be understood to include the possibilities of "A" or "B" or "A and B."

Various operations may be described as multiple discrete operations in turn, in a manner that may be helpful in understanding embodiments; however, the order of description should not be construed to imply that these operations are order-dependent. Also, embodiments may have fewer operations than described. A description of multiple discrete operations should not be construed to imply that all operations are necessary. Also, embodiments may have fewer operations than described. A description of multiple discrete operations should not be construed to imply that all operations are necessary.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the disclosure. Those with skill in the art will readily appreciate that embodiments of the disclosure may be implemented in a very wide variety of ways. This disclosure is intended to cover any adaptations or variations of the embodiments discussed herein. Therefore, it is manifestly intended that embodiments of the disclosure be limited only by the claims and the equivalents thereof.

What is claimed is:

1. A method for biopatterning a biological target, the method including:
   obtaining a radiation pattern to be applied to an area of the biological target, wherein the biological target includes a first group of photosensitive elements, and wherein the first group of photosensitive elements is responsive to a first activation wavelength;
   radiating a first light beam of a first shape into the area of the biological target, wherein the first light beam includes a first radiation dose including the first activation wavelength, and wherein the first radiation dose does not satisfy an activation threshold for activating the first group of photosensitive elements;
   radiating a second light beam of a second shape into the area of the biological target, wherein the second light beam includes a second radiation dose including the first activation wavelength, wherein the second radiation dose does not satisfy the activation threshold, and wherein a combination of the first dose and the second dose satisfies the activation threshold; and
   activating the first group of photosensitive elements located within an intersection of the first light beam and the second light beam in the area of the biological target responsive to satisfaction of the activation threshold, wherein the intersection of the first light beam and the second light beam has a contour that matches at least a portion of the radiation pattern.

2. The method of claim 1, further including:
   selecting, from an image of the biological target, one or more contours of the area in which the radiation pattern is to be applied.

3. The method of claim 2, further including:
   scanning the biological target to generate scan data; and
   generating the image of the biological target based on the scan data.

4. The method of claim 2, wherein said obtaining the radiation pattern comprises selecting the one or more contours of the area, and wherein the radiation pattern is defined by the one or more contours.

5. The method of claim 1, wherein the radiation pattern comprises a three-dimensional (3D) pattern, and wherein the contour of the intersection matches at least a portion of the 3D pattern.

6. The method of claim 1, wherein the first activation wavelength is in the range of 1 mm to 760 nm, 760 nm to 380 nm, or 380 nm to 10 nm.

7. The method of claim 1, wherein the first group of photosensitive elements located within the intersection is activated to adhere to the biological target.

8. The method of claim 1, wherein the first group of photosensitive elements located within the intersection is activated to adhere to the biological target to form a 3D structure in the area of the biological target.

9. The method of claim 1, wherein the first group of photosensitive elements comprises photo-adhesive molecules, photo-adhesive biochemical factors, or nanoparticles.

10. The method of claim 1, wherein the biological target comprises a tissue, an organ, or a scaffold.

11. The method of claim 1, wherein at least some of the first group of photosensitive elements are each coupled to one or more biochemical factors, and wherein the photosensitive elements are configured to release the one or more biochemical factors in response to radiation of the first activation wavelength.

12. The method of claim 11, wherein the one or more biochemical factors comprises a growth factor, a nucleic acid molecule, a ribonucleic acid molecule, or a protein.

13. The method of claim 1, wherein the first group of photosensitive elements includes nanoparticles, and wherein a targeting molecule is coupled to an outer surface of a particular nanoparticle.

14. The method of claim 1, wherein the biological target further includes a second group of photosensitive elements, and wherein the second group of photosensitive elements is responsive to a second activation wavelength, the method further including:
   radiating a third light beam of a third shape into the area of the biological target, wherein the third light beam includes a third radiation dose including the second activation wavelength, and wherein the third radiation dose does not satisfy a second activation threshold for activating the second group of photosensitive elements;

radiating a fourth light beam of a fourth shape into the area of the biological target, wherein the fourth light beam includes a fourth radiation dose including the second activation wavelength, wherein the fourth radiation dose does not satisfy the second activation threshold, and wherein a combination of the third dose and the fourth dose satisfies the second activation threshold; and activating the second group of photosensitive elements located within a second intersection of the third light beam and the fourth light beam in the area of the biological target, wherein the second intersection has a contour that matches at least another portion of the radiation pattern.

15. The method of claim 1, wherein the obtaining is performed by a computing source, wherein the radiating the first light beam is performed by a first radiation source, wherein the radiating the second light beam is performed by a second radiation source.

\* \* \* \* \*